(12) United States Patent
Yu

(10) Patent No.: US 9,566,201 B2
(45) Date of Patent: Feb. 14, 2017

(54) MOUNTING SUPPORT ASSEMBLY FOR SUSPENDING A MEDICAL INSTRUMENT DRIVER ABOVE AN OPERATING TABLE

(71) Applicant: Hansen Medical, Inc., Mountain View, CA (US)

(72) Inventor: Alan L Yu, Union City, CA (US)

(73) Assignee: HANSEN MEDICAL, INC., Mountain View, CA (US)

(*) Notice: Subject to any disclaimer, the term of this patent is extended or adjusted under 35 U.S.C. 154(b) by 855 days.

(21) Appl. No.: 13/910,903

(22) Filed: Jun. 5, 2013

(65) Prior Publication Data
US 2013/0269109 A1 Oct. 17, 2013

Related U.S. Application Data

(63) Continuation of application No. 13/437,716, filed on Apr. 2, 2012, now abandoned, which is a continuation
(Continued)

(51) Int. Cl.
*A61G 7/05* (2006.01)
*A61G 13/10* (2006.01)
*A61B 17/00* (2006.01)

(52) U.S. Cl.
CPC .............. *A61G 7/0503* (2013.01); *A61B 34/20* (2016.02); *A61B 34/30* (2016.02); *A61B 34/71* (2016.02);
(Continued)

(58) Field of Classification Search
CPC .......... A61G 7/065; A61G 7/07; A61G 7/072; A61G 7/075; A61G 7/0755; A61G 13/10; A61G 13/101; A61G 13/12; A61G 13/1205; A61G 13/121; A61G 13/122; A61G 13/1225; A61G 13/123; A61G 13/1235; A61G 13/124; A61G 13/1245; A61G 13/125; A61G 13/1255
(Continued)

(56) References Cited

U.S. PATENT DOCUMENTS 1,598,569 A 8/1926 Fitzhugh
2,048,449 A 7/1936 Holtzman
(Continued)

FOREIGN PATENT DOCUMENTS

EP 1103223 A2 5/2001
EP 1290982 3/2003
(Continued)

OTHER PUBLICATIONS

PCT International Search Report and Written Opinion of the International Search Authority for PCT/US2008/052814, Applicant Hansen Medical, Inc., Forms PCT/ISA/210, 220, and 237, dated Sep. 2, 2008 (11 pages).
(Continued)

*Primary Examiner* — Robert G Santos
(74) *Attorney, Agent, or Firm* — Dorsey & Whitney LLP

(57) ABSTRACT

An adjustable mounting assembly, includes a load distributing plate configured for resting on, and being supported by, a top surface of a patient table; a first clamp assembly adjustably coupled to a first side of the load distributing plate and configured for removable attachment to a first side rail of the patient table; a second clamp assembly coupled to a second side of the load distributing plate and configured for removable attachment to a second side rail of the patient table; and an adapter rail fixed to the second side of the load distributing plate and configured to detachably couple to a support assembly interface, such that an adjustable support assembly may be coupled to the load distributing plate to thereby allow for an off-center load attached to the support
(Continued)

assembly to be moved relative to the patient table while the load remains substantially supported by the table surface.

20 Claims, 18 Drawing Sheets

Related U.S. Application Data of application No. 12/024,883, filed on Feb. 1, 2008, now Pat. No. 8,146,874.

(60) Provisional application No. 60/900,584, filed on Feb. 8, 2007, provisional application No. 60/899,048, filed on Feb. 2, 2007.

(52) U.S. Cl.
CPC ........... *A61G 13/101* (2013.01); *A61B 90/361* (2016.02); *A61B 90/50* (2016.02); *A61B 2017/00261* (2013.01); *A61B 2034/102* (2016.02); *A61B 2034/2051* (2016.02); *A61B 2034/2061* (2016.02); *A61G 13/10* (2013.01)

(58) Field of Classification Search
USPC ..................... 5/621–624, 636, 640, 646–651
See application file for complete search history.

(56) References Cited

U.S. PATENT DOCUMENTS

| | | | |
|---|---|---|---|
| 2,452,816 A | 11/1948 | Wagner | |
| 2,466,518 A | 4/1949 | Wagner | |
| 2,535,559 A | 12/1950 | Monroe | |
| 2,569,729 A | 10/1951 | Nold | |
| 2,788,529 A | 4/1957 | Moritzacky et al. | |
| 2,940,715 A | 6/1960 | Schultz et al. | |
| 2,970,798 A | 2/1961 | Fritchle et al. | |
| 3,495,519 A | 2/1970 | Alfsen et al. | |
| 3,823,709 A * | 7/1974 | McGuire | A61B 17/0293 |
| | | | 128/850 |
| 3,844,550 A * | 10/1974 | McGuire | A61B 17/0293 |
| | | | 128/845 |
| 4,099,521 A | 7/1978 | Nestor et al. | |
| 4,151,812 A | 5/1979 | Miller | |
| 4,180,254 A | 12/1979 | Lee et al. | |
| 4,355,631 A * | 10/1982 | LeVahn | A61B 17/0293 |
| | | | 600/230 |
| 4,432,525 A | 2/1984 | Duvall | |
| 4,545,573 A | 10/1985 | Murphy | |
| 4,559,942 A | 12/1985 | Eisenberg | |
| 4,583,539 A | 4/1986 | Karlin et al. | |
| 4,583,725 A * | 4/1986 | Arnold | A61G 13/12 |
| | | | 5/621 |
| 4,729,336 A | 3/1988 | Rohne | |
| 4,766,838 A | 8/1988 | Johnson | |
| 4,773,709 A | 9/1988 | Slinkard | |
| 4,886,258 A | 12/1989 | Scott | |
| 4,930,523 A | 6/1990 | Laico et al. | |
| 4,971,037 A * | 11/1990 | Pelta | A61B 17/0206 |
| | | | 403/390 |
| 5,025,802 A | 6/1991 | Laico et al. | |
| 5,112,015 A | 5/1992 | Williams | |
| 5,290,220 A | 3/1994 | Guhl | |
| 5,330,147 A | 7/1994 | Volcheff et al. | |
| 5,400,772 A * | 3/1995 | LeVahn | A61B 17/02 |
| | | | 248/316.1 |
| 5,423,798 A | 6/1995 | Crow | |
| 5,462,551 A | 10/1995 | Bailey et al. | |
| 5,492,131 A | 2/1996 | Galel | |
| 5,590,619 A | 1/1997 | Meador et al. | |
| 5,722,959 A | 3/1998 | Bierman | |
| 5,845,646 A | 12/1998 | Lemelson | |
| 5,855,583 A * | 1/1999 | Wang | A61B 34/75 |
| | | | 318/568.11 |
| 5,876,325 A | 3/1999 | Mizuno et al. | |
| 5,925,078 A | 7/1999 | Anderson | |
| 5,926,876 A | 7/1999 | Haigh et al. | |
| 5,960,746 A | 10/1999 | Salts | |
| 6,004,271 A | 12/1999 | Moore | |
| 6,007,550 A * | 12/1999 | Wang | A61B 34/75 |
| | | | 318/568.11 |
| 6,061,587 A | 5/2000 | Kucharczyk et al. | |
| 6,070,584 A | 6/2000 | Bergstrom | |
| 6,102,850 A * | 8/2000 | Wang | A61B 34/75 |
| | | | 414/2 |
| 6,129,668 A | 10/2000 | Haynor et al. | |
| 6,154,901 A | 12/2000 | Carr | |
| 6,189,478 B1 | 2/2001 | Myers et al. | |
| 6,203,493 B1 | 3/2001 | Ben-Haim | |
| 6,363,279 B1 | 3/2002 | Ben-Haim et al. | |
| 6,381,483 B1 | 4/2002 | Hareyama et al. | |
| 6,436,107 B1 * | 8/2002 | Wang | A61B 1/00149 |
| | | | 318/568.11 |
| 6,475,223 B1 | 11/2002 | Werp et al. | |
| 6,499,158 B1 * | 12/2002 | Easterling | A61G 15/10 |
| | | | 248/231.61 |
| 6,530,913 B1 | 3/2003 | Giba et al. | |
| 6,544,230 B1 | 4/2003 | Flaherty et al. | |
| 6,551,273 B1 | 4/2003 | Olson et al. | |
| 6,564,406 B2 | 5/2003 | VanSteenburg et al. | |
| 6,598,275 B1 * | 7/2003 | Kolody | A61G 13/101 |
| | | | 24/455 |
| 6,610,007 B2 | 8/2003 | Belson et al. | |
| 6,629,534 B1 | 10/2003 | St. Goar et al. | |
| 6,669,709 B1 | 12/2003 | Cohn et al. | |
| 6,671,904 B2 * | 1/2004 | Easterling | A61G 15/10 |
| | | | 108/27 |
| 6,699,177 B1 * | 3/2004 | Laby | A61B 34/75 |
| | | | 414/2 |
| 6,743,221 B1 | 6/2004 | Hobart et al. | |
| 6,800,076 B2 | 10/2004 | Humayun | |
| 6,804,846 B2 | 10/2004 | Schuerch | |
| 6,820,621 B2 * | 11/2004 | DeMayo | A61B 13/12 |
| | | | 128/845 |
| 6,905,460 B2 | 6/2005 | Wang et al. | |
| 6,912,959 B2 * | 7/2005 | Kolody | A61G 13/101 |
| | | | 108/27 |
| 7,020,917 B1 * | 4/2006 | Kolody | A61B 6/0442 |
| | | | 108/28 |
| 7,022,109 B1 | 4/2006 | Ditto | |
| 7,025,064 B2 * | 4/2006 | Wang | A61B 34/75 |
| | | | 128/898 |
| 7,083,571 B2 * | 8/2006 | Wang | A61B 34/75 |
| | | | 414/2 |
| 7,118,582 B1 * | 10/2006 | Wang | A61B 34/75 |
| | | | 318/568.1 |
| 7,143,458 B2 | 12/2006 | Slater, Jr. | |
| 7,156,806 B2 | 1/2007 | Dobrovolny | |
| 7,159,832 B2 * | 1/2007 | Easterling | A61G 15/10 |
| | | | 24/455 |
| 7,167,622 B2 | 1/2007 | Temelkuran et al. | |
| 7,201,747 B2 | 4/2007 | Edoga et al. | |
| 7,280,863 B2 | 10/2007 | Shachar | |
| 7,371,210 B2 | 5/2008 | Brock et al. | |
| 7,380,299 B1 | 6/2008 | DeMayo | |
| 7,404,824 B1 | 7/2008 | Webler et al. | |
| 7,695,481 B2 * | 4/2010 | Wang | A61B 34/75 |
| | | | 414/2 |
| 7,789,874 B2 | 9/2010 | Yu et al. | |
| 7,850,642 B2 | 12/2010 | Moll et al. | |
| 7,914,521 B2 * | 3/2011 | Wang | A61B 34/75 |
| | | | 414/2 |
| 7,922,693 B2 * | 4/2011 | Reis | A61B 19/2203 |
| | | | 604/118 |
| 7,963,288 B2 | 6/2011 | Rosenberg et al. | |
| 7,972,298 B2 | 7/2011 | Wallace et al. | |
| 7,974,681 B2 * | 7/2011 | Wallace | 600/114 |
| 7,976,539 B2 * | 7/2011 | Hlavka | A61B 18/1492 |
| | | | 128/898 |
| 8,005,537 B2 * | 8/2011 | Hlavka | A61B 18/1492 |
| | | | 600/114 |

(56) References Cited

U.S. PATENT DOCUMENTS

| | | | |
|---|---|---|---|
| 8,021,326 B2 | 9/2011 | Moll et al. | |
| 8,041,413 B2* | 10/2011 | Barbagli | A61B 5/06 600/424 |
| 8,052,636 B2 | 11/2011 | Moll et al. | |
| 8,108,069 B2* | 1/2012 | Stahler | A61B 17/12122 700/245 |
| 8,146,874 B2 | 4/2012 | Yu | |
| 8,190,238 B2 | 5/2012 | Moll et al. | |
| 8,196,238 B2 | 6/2012 | Hejkal et al. | |
| 8,230,864 B2* | 7/2012 | Hunter, Jr. | A61F 5/3761 128/845 |
| 8,285,364 B2* | 10/2012 | Barbagli | A61B 5/06 600/424 |
| 8,317,746 B2* | 11/2012 | Sewell | A61B 19/201 600/114 |
| 8,377,077 B2* | 2/2013 | Reis | A61B 19/2203 606/130 |
| 8,391,957 B2* | 3/2013 | Carlson | A61B 19/2203 600/429 |
| 8,409,172 B2* | 4/2013 | Moll | A61B 1/00082 128/898 |
| 8,409,234 B2* | 4/2013 | Stahler | 606/170 |
| 8,498,691 B2* | 7/2013 | Moll | A61B 17/0057 600/411 |
| 8,657,781 B2* | 2/2014 | Sewell | A61B 19/201 600/114 |
| 8,671,817 B1* | 3/2014 | Bogusky | D04C 3/48 87/35 |
| 8,672,837 B2* | 3/2014 | Roelle | A61B 1/00006 600/117 |
| 8,720,448 B2* | 5/2014 | Reis | 128/852 |
| 8,827,948 B2* | 9/2014 | Romo | A61B 6/12 604/95.04 |
| 8,864,655 B2* | 10/2014 | Ramamurthy | A61B 5/06 600/117 |
| 8,894,610 B2* | 11/2014 | MacNamara | A61M 25/0147 604/95.04 |
| 8,961,533 B2* | 2/2015 | Stahler | A61B 6/12 606/108 |
| 8,968,333 B2* | 3/2015 | Yu | A61B 19/26 248/349.1 |
| 8,989,528 B2* | 3/2015 | Udd | A61B 5/06 385/10 |
| 9,014,851 B2* | 4/2015 | Wong | A61B 19/2203 600/104 |
| 9,023,068 B2 | 5/2015 | Viola | |
| 9,039,685 B2 | 5/2015 | Larkin et al. | |
| 9,057,600 B2* | 6/2015 | Walker | G01B 11/14 |
| 9,066,740 B2* | 6/2015 | Carlson | A61B 19/2203 |
| 9,161,772 B2* | 10/2015 | Hyodo | B25J 13/02 |
| 9,186,046 B2* | 11/2015 | Ramamurthy | A61B 5/06 |
| 9,186,047 B2* | 11/2015 | Ramamurthy | A61B 5/06 |
| 9,244,524 B2* | 1/2016 | Inoue | A61B 19/2203 |
| 9,254,123 B2* | 2/2016 | Alvarez | A61B 17/00234 |
| 9,289,578 B2* | 3/2016 | Walker | A61M 25/0108 |
| 2001/0009976 A1 | 7/2001 | Panescu et al. | |
| 2001/0021843 A1 | 9/2001 | Bosselmann et al. | |
| 2001/0029366 A1 | 10/2001 | Swanson et al. | |
| 2001/0055016 A1 | 12/2001 | Krishnan | |
| 2002/0007144 A1 | 1/2002 | Snoke | |
| 2002/0087169 A1 | 7/2002 | Brock et al. | |
| 2002/0091374 A1 | 7/2002 | Cooper | |
| 2002/0138009 A1 | 9/2002 | Brockway et al. | |
| 2002/0156369 A1 | 10/2002 | Chakeres | |
| 2002/0161446 A1 | 10/2002 | Bryan et al. | |
| 2002/0177789 A1 | 11/2002 | Ferry et al. | |
| 2003/0055418 A1 | 3/2003 | Tasto et al. | |
| 2003/0061660 A1* | 4/2003 | Easterling | A61G 15/10 5/600 |
| 2003/0073908 A1 | 4/2003 | Desai | |
| 2003/0074011 A1 | 4/2003 | Gilboa et al. | |
| 2003/0083648 A1* | 5/2003 | Wang | A61B 34/75 606/1 |
| 2003/0100817 A1* | 5/2003 | Wang | A61B 34/75 600/102 |
| 2003/0125716 A1* | 7/2003 | Wang | A61B 34/75 606/1 |
| 2003/0135204 A1 | 7/2003 | Lee et al. | |
| 2003/0155478 A1* | 8/2003 | Easterling | A61G 15/10 248/316.1 |
| 2003/0178027 A1* | 9/2003 | DeMayo | A61G 13/12 128/845 |
| 2003/0205176 A1* | 11/2003 | Kolody | A61G 13/101 108/28 |
| 2004/0106916 A1 | 6/2004 | Quaid et al. | |
| 2004/0165810 A1 | 8/2004 | Fujita | |
| 2004/0176751 A1 | 9/2004 | Weitzner et al. | |
| 2004/0186345 A1* | 9/2004 | Yang | A61B 34/75 600/102 |
| 2004/0193146 A1 | 9/2004 | Lee et al. | |
| 2004/0220588 A1 | 11/2004 | Kermode et al. | |
| 2005/0045785 A1 | 3/2005 | Cohen | |
| 2005/0137478 A1 | 6/2005 | Younge et al. | |
| 2005/0159789 A1 | 7/2005 | Brockway et al. | |
| 2005/0171553 A1 | 8/2005 | Schwarz et al. | |
| 2005/0182295 A1 | 8/2005 | Soper et al. | |
| 2005/0182330 A1 | 8/2005 | Brockway et al. | |
| 2005/0197530 A1 | 9/2005 | Wallace et al. | |
| 2005/0203382 A1 | 9/2005 | Govari et al. | |
| 2005/0222554 A1* | 10/2005 | Wallace | A61B 8/12 606/1 |
| 2005/0228365 A1* | 10/2005 | Wang | A61B 34/75 606/1 |
| 2006/0013523 A1 | 1/2006 | Childers et al. | |
| 2006/0025676 A1 | 2/2006 | Viswanathan et al. | |
| 2006/0057560 A1* | 3/2006 | Hlavka | A61B 18/1492 435/4 |
| 2006/0058647 A1 | 3/2006 | Strommer et al. | |
| 2006/0084945 A1 | 4/2006 | Moll et al. | |
| 2006/0094956 A1 | 5/2006 | Viswanathan | |
| 2006/0095022 A1 | 5/2006 | Moll et al. | |
| 2006/0100610 A1 | 5/2006 | Wallace et al. | |
| 2006/0111692 A1 | 5/2006 | Hlavka et al. | |
| 2006/0167441 A1* | 7/2006 | Wang | A61B 34/75 606/1 |
| 2006/0200026 A1 | 9/2006 | Wallace et al. | |
| 2006/0253108 A1 | 11/2006 | Yu et al. | |
| 2006/0271036 A1 | 11/2006 | Garabedian et al. | |
| 2006/0276775 A1 | 12/2006 | Rosenberg et al. | |
| 2006/0293643 A1 | 12/2006 | Wallace et al. | |
| 2007/0038181 A1 | 2/2007 | Melamud et al. | |
| 2007/0043338 A1 | 2/2007 | Moll et al. | |
| 2007/0060879 A1 | 3/2007 | Weitzner et al. | |
| 2007/0094798 A1 | 5/2007 | Yu | |
| 2007/0156019 A1 | 7/2007 | Larkin et al. | |
| 2007/0156123 A1 | 7/2007 | Moll et al. | |
| 2007/0197896 A1 | 8/2007 | Moll et al. | |
| 2007/0249901 A1 | 10/2007 | Ohline et al. | |
| 2008/0058836 A1* | 3/2008 | Moll | A61B 1/00082 606/130 |
| 2008/0119727 A1* | 5/2008 | Barbagli | A61B 5/06 600/424 |
| 2008/0167750 A1* | 7/2008 | Stahler | A61B 17/12122 700/245 |
| 2008/0183071 A1 | 7/2008 | Strommer et al. | |
| 2008/0195081 A1 | 8/2008 | Moll | |
| 2008/0215065 A1* | 9/2008 | Wang | A61B 34/75 606/130 |
| 2008/0218770 A1 | 9/2008 | Moll et al. | |
| 2008/0228196 A1* | 9/2008 | Wang | A61B 34/75 606/130 |
| 2008/0234631 A1* | 9/2008 | Reis | A61B 19/2203 604/122 |
| 2008/0245946 A1 | 10/2008 | Yu | |
| 2008/0255505 A1* | 10/2008 | Carlson | A61B 19/2203 604/95.04 |
| 2008/0275367 A1 | 11/2008 | Barbagli et al. | |
| 2008/0300592 A1 | 12/2008 | Weitzner et al. | |
| 2008/0319311 A1 | 12/2008 | Hamadeh | |
| 2009/0024141 A1* | 1/2009 | Stahler | 606/130 |
| 2009/0036900 A1 | 2/2009 | Moll | |

(56) References Cited

U.S. PATENT DOCUMENTS

| | | | |
|---|---|---|---|
| 2009/0054884 A1 | 2/2009 | Farley et al. | |
| 2009/0123111 A1* | 5/2009 | Udd | A61B 5/06 385/13 |
| 2009/0137952 A1 | 5/2009 | Ramamurthy et al. | |
| 2009/0138025 A1 | 5/2009 | Stahler et al. | |
| 2009/0221908 A1 | 9/2009 | Glossop | |
| 2009/0318797 A1 | 12/2009 | Hadani | |
| 2010/0010504 A1 | 1/2010 | Simaan et al. | |
| 2010/0081920 A1 | 4/2010 | Whitmore, III et al. | |
| 2010/0125285 A1* | 5/2010 | Sewell | A61B 19/201 606/130 |
| 2010/0170519 A1* | 7/2010 | Romo | 128/852 |
| 2010/0205740 A1 | 8/2010 | Tybinkowski et al. | |
| 2010/0280449 A1* | 11/2010 | Alvarez | A61B 17/00234 604/95.04 |
| 2010/0308195 A1* | 12/2010 | Yu | A61B 19/26 248/349.1 |
| 2011/0048428 A1* | 3/2011 | Hunter, Jr. | A61F 5/3761 128/845 |
| 2011/0087238 A1* | 4/2011 | Wang | A61B 34/75 606/130 |
| 2011/0152883 A1* | 6/2011 | Reis | A61B 19/2203 606/130 |
| 2011/0319714 A1* | 12/2011 | Roelle | A61B 1/00006 600/118 |
| 2012/0035481 A1* | 2/2012 | Barbagli | A61B 5/06 600/443 |
| 2012/0071821 A1* | 3/2012 | Yu | A61B 6/12 604/95.01 |
| 2012/0071822 A1* | 3/2012 | Romo | A61B 6/12 604/95.04 |
| 2012/0071895 A1* | 3/2012 | Stahler | A61B 6/12 606/130 |
| 2012/0209293 A1* | 8/2012 | Carlson | A61B 19/2203 606/130 |
| 2012/0241576 A1 | 9/2012 | Yu | |
| 2012/0253332 A1 | 10/2012 | Moll | |
| 2013/0066333 A1* | 3/2013 | Hyodo | B25J 13/02 606/130 |
| 2013/0072944 A1* | 3/2013 | Sewell | A61B 19/201 606/130 |
| 2013/0085334 A1* | 4/2013 | Ramamurthy | A61B 5/06 600/117 |
| 2013/0090530 A1* | 4/2013 | Ramamurthy | A61B 5/06 600/182 |
| 2013/0269109 A1* | 10/2013 | Yu | A61G 7/0503 5/503.1 |
| 2014/0148759 A1* | 5/2014 | MacNamara | A61M 25/0147 604/95.04 |
| 2014/0148819 A1* | 5/2014 | Inoue | A61B 19/2203 606/130 |
| 2014/0264081 A1* | 9/2014 | Walker | G01B 11/14 250/459.1 |
| 2014/0276647 A1* | 9/2014 | Yu | A61B 19/2203 604/528 |
| 2014/0276935 A1* | 9/2014 | Yu | A61B 19/2203 606/130 |
| 2014/0276937 A1* | 9/2014 | Wong | A61B 19/2203 606/130 |
| 2014/0276939 A1* | 9/2014 | Kokish | A61B 19/2203 606/130 |
| 2014/0277333 A1* | 9/2014 | Lewis | A61B 19/2203 623/1.11 |
| 2014/0277334 A1* | 9/2014 | Yu | A61B 19/2203 623/1.11 |
| 2015/0133858 A1 | 5/2015 | Julian et al. | |
| 2015/0246204 A1* | 9/2015 | Walker | G01B 11/14 73/1.79 |

FOREIGN PATENT DOCUMENTS

| | | |
|---|---|---|
| TW | M296033 | 8/2006 |
| WO | 03086190 A1 | 10/2003 |
| WO | 2008097540 A2 | 8/2008 |
| WO | 2008097853 A2 | 8/2008 |
| WO | 2014/028699 A1 | 2/2014 |
| WO | 2014/028702 A1 | 2/2014 |

OTHER PUBLICATIONS

Fleishman-Hillard, Inc., "Magnetic Surgery System Tested Successfully on First Patient", Science Blog., Dec. 22, 1998. [Retrieved Jan. 8, 2015] http://scienceblog.com/community/older/1998/B/199801237.html. (4 pages).

Grace et al., "A Six Degree of Freedom Micromanipulator for Ophthalmic Surgery", Proceedings IEEE International Conference on Robotics and Automation; vol. 1; May 1993; pp. 630-635. (6 pages).

Hunter et al., "Ophthalmic Microsurgical Robot and Associated Virtual Environment", Computers in Biology Med.; vol. 25, No. 2, 1995, pp. 173-182. (10 pages).

\* cited by examiner

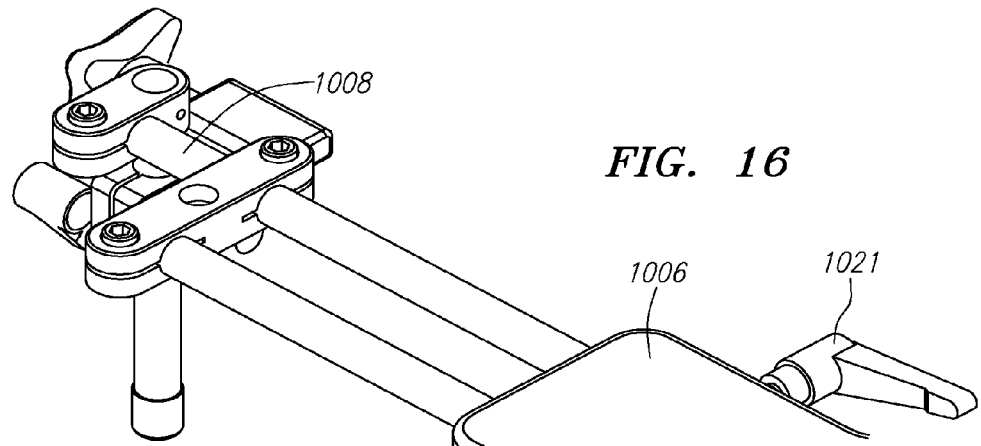
FIG. 16
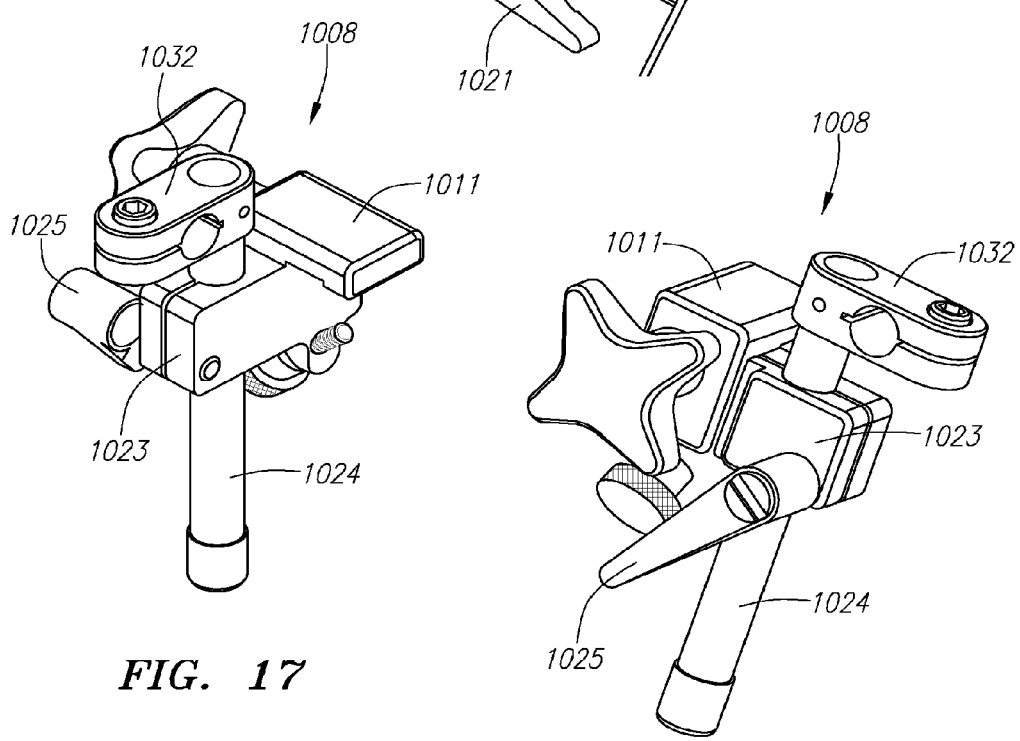
FIG. 17
FIG. 18

US 9,566,201 B2

MOUNTING SUPPORT ASSEMBLY FOR SUSPENDING A MEDICAL INSTRUMENT DRIVER ABOVE AN OPERATING TABLE

RELATED APPLICATION DATA

The present application is a continuation of U.S. patent application Ser. No. 13/437,716, filed Apr. 2, 2012, which is a continuation of U.S. patent application Ser. No. 12/024,883, now issued U.S. Pat. No. 8,146,874, filed Feb. 1, 2008, which claims the benefit under 35 U.S.C. §119 to U.S. Provisional Patent Application Ser. Nos. 60/899,048, filed on Feb. 2, 2007, and 60/900,584, filed on Feb. 8, 2007. The foregoing applications are hereby incorporated by reference into the present application in their entirety.

FIELD OF INVENTION

The invention relates generally to robotically controlled medical instrument systems, such as telerobotic surgical systems, and more particularly to a mounting support assembly for suspending a robotically controlled instrument driver over an operating table for performing minimally invasive diagnostic and therapeutic medical procedures.

BACKGROUND

Robotic interventional systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be accessed via naturally-occurring pathways such as blood vessels, other lumens, via surgically-created wounds of minimized size, or combinations thereof.

SUMMARY OF THE INVENTION

The present invention is directed to an adapter plate assembly which provides a convenient interface between a mounting support assembly for suspending an instrument driver of robotic instrument system above an operating table. The adapter plate securely mounts to the operating table, and may be adjustable so that it can be adjusted to fit various sizes and models of operating tables. Then, a component of the robotic instrument system, such as a support assembly having a plurality of adjustable arms for supporting an instrument, may be secured to the adapter plate assembly.

In one embodiment, an adjustable mounting assembly for suspending an off-center load above a patient table includes a load distributing plate configured for resting on, and being supported by, a top surface of the patient table. A first clamp assembly is adjustably coupled to a first side of the load distributing plate and configured for removable attachment to a first side rail of the patient table. By way of non-limiting example, the first clamp assembly may be mounted on one or more adjustment rods that are slidably received in the first side of the load distributing plate so that the first clamp assembly may be extended from, and retracted into, the load distributing plate so as to adjust a width of the mounting assembly to accommodate a width of the patient table. Respective locking devices may be provided for securing the one or more adjustment rods in a desired position relative to the load distributing plate. A second clamp assembly is coupled to a second side of the load distributing plate and configured for removable attachment to a second side rail of the patient table. By way of non-limiting examples, the first and second clamp assemblies may each comprise an L-shaped clamp body configured to engage the respective side rail of the patient table. An adapter rail is fixed to the second side of the load distributing plate and configured to detachably couple to a support assembly interface, such that an adjustable support assembly may be coupled to the load distributing plate to thereby allow for an off-center load attached to the support assembly to be moved relative to the patient table while the load remains substantially supported by the table surface.

In another embodiment, an adjustable mounting assembly for suspending an off-center load above a patient table includes a load distributing plate configured for resting on, and being supported by, a top surface of the patient table. A first clamp assembly configured for removable attachment to a first side rail of the patient table is mounted on one or more adjustment rods that are slidably received in a first side of the load distributing plate to thereby allow the first clamp assembly to be extended from, and retracted into, the load distributing plate so as to adjust a width of the mounting assembly to accommodate a width of the patient table. Respective locking devices may be provided for securing the one or more adjustment rods in a desired position relative to the load distributing plate. A second clamp assembly is coupled to a second side of the load distributing plate, and a third clamp assembly is also coupled to the second side of the load distributing plate at a location spaced apart from the second clamp assembly, wherein the second and third clamp assemblies are configured for removable attachment to the second side rail of the patient table. By way of non-limiting examples, the first, second and third clamp assemblies may each comprise an L-shaped clamp body configured to engage the respective side rail of the patient table. An adapter rail is fixed to the second side of the load distributing plate and configured to detachably couple to a support assembly interface, such that an adjustable support assembly may be coupled to the load distributing plate to thereby allow for an off-center load attached to the support assembly to be moved relative to the patient table while the load remains substantially supported by the table surface.

BRIEF DESCRIPTION OF THE DRAWINGS

The drawings illustrate the design and utility of illustrated embodiments of the invention, in which similar elements are referred to by common reference numerals.

FIGS. 9A-10 illustrate one embodiment of a clamp assembly;

FIG. 16 illustrates an enlarged view of the portion of one embodiment of an adapter plate assembly near the surgeon side;

FIGS. 17-18 illustrate one embodiment of clamp assemblies;

DETAILED DESCRIPTION OF THE ILLUSTRATED EMBODIMENTS

The present invention is directed to various embodiments of mounting platforms for mounting an instrument driver of a robotic instrument system to an operating table. The mounting platform, along with the mounted support assembly can be used to support and adjust the position of the instrument driver on or near an operating table. It is to be understood that each of the embodiments described herein may be utilized with robotic instrument systems, which can control the positioning of the devices within a patients body, and may also control the operation of other functions of the devices, such as imaging devices, ablation devices, cutting tools, or other end effectors, including without limitation all of the robotic instrument systems incorporated by reference below.

Figure 1A:
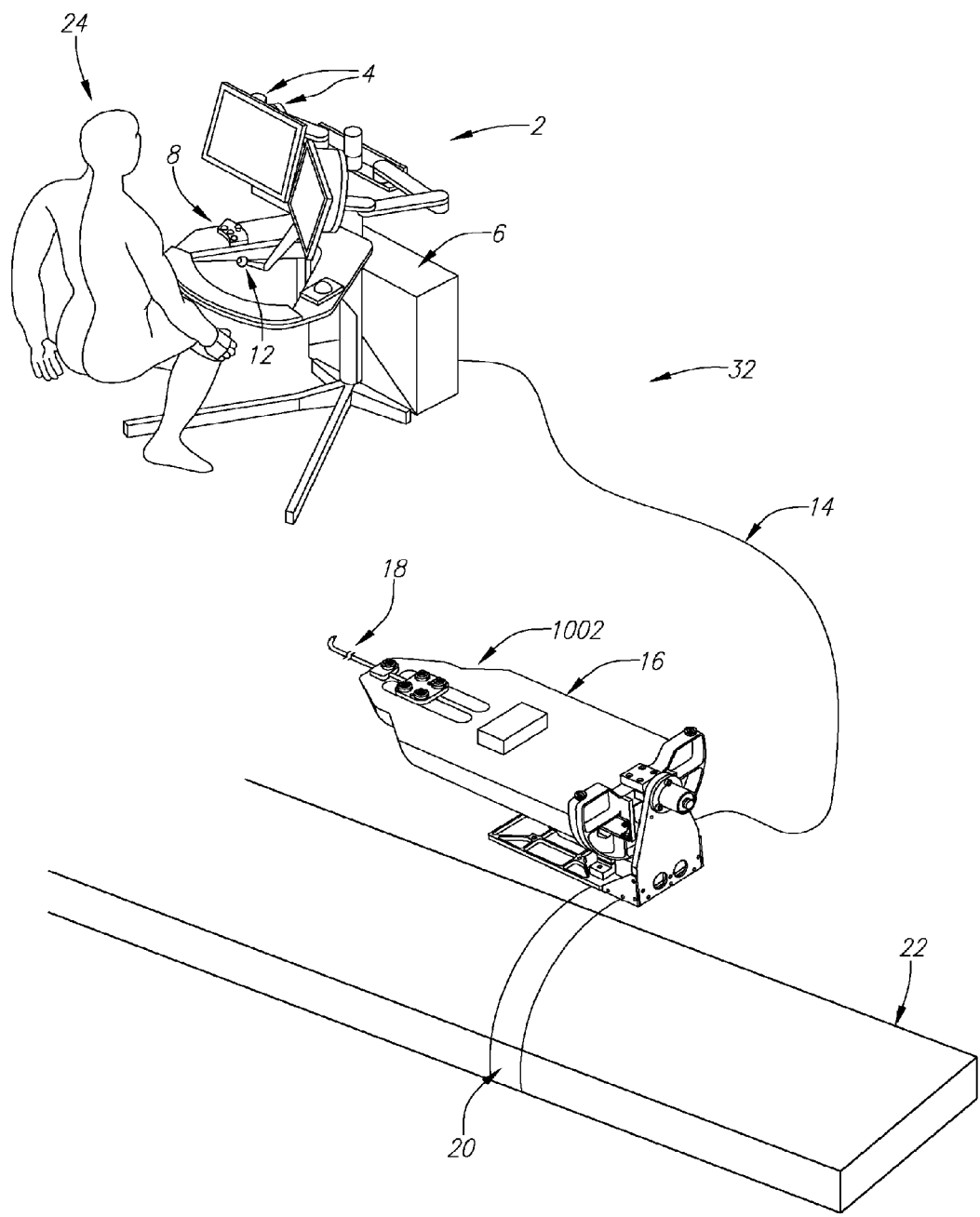
FIG. 1A illustrates a one embodiment of a robotic instrument system.

Referring to FIG. 1A, one embodiment of a robotic instrument system (32), includes an operator control station (2) located remotely from an operating table (22), and a robotic instrument assembly (1002). The robotic instrument assembly (1002) comprises an instrument driver (16) and an instrument (18) coupled to the operating table (22) by an instrument driver mounting brace (20). A communication link (14) transfers signals between the operator control station (2) and instrument driver (16). The instrument driver mounting brace (20) of the depicted embodiment is a relatively simple, arcuate-shaped structural member configured to position the instrument driver (16) above a patient (not shown) lying on the table (22).

Figure 1B:
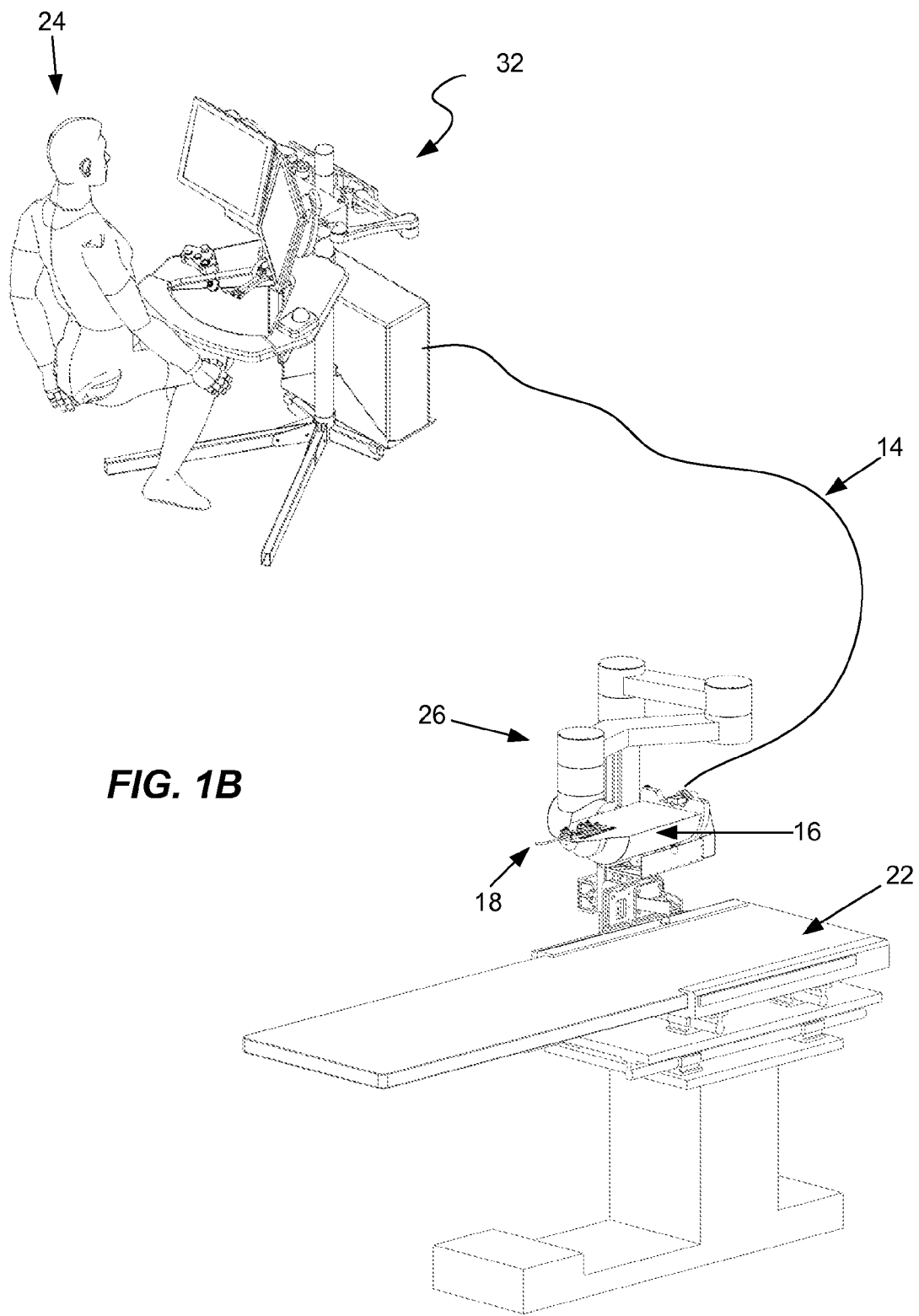
FIG. 1B illustrates another embodiment of a robotic instrument system.

In FIG. 1B, another embodiment of a robotic instrument system (32) is depicted, wherein the arcuate-shaped member (20) is replaced by a movable support assembly (26). The support assembly (26) is configured to movably support the instrument driver (16) above the operating table (22) in order to position the instrument driver (16) for convenient access into desired locations relative to a patient (not shown). The support assembly (26) in FIG. 1B is also configured to lock the instrument driver (16) into position once it is positioned.

The instrument (18) is typically an elongate, flexible device configured to be inserted into a patient's body. As non-limiting examples, an instrument (18) may comprise an intravascular catheter, an endoscopic surgical instrument or other medical instrument. The instrument (18) may also comprise an instrument assembly (28) comprising a robotic guide instrument (18), or a coaxially coupled and independently controllable robotic sheath instrument and a robotic guide instrument (18), as described in the U.S. Patent Applications incorporated by reference below. The instrument (18) or instrument assembly (28) is configured to be operable via the instrument driver (16) such that the instrument driver (16) can operate to steer the instrument (18) or instrument assembly (28) and also to operate tools and devices which may be provided on the instrument assembly (18) or instrument assembly (28) (e.g. an imaging device or cutting tool disposed on the distal end of the instrument (18) or instrument assembly (28)). Alternatively, manually steerable and operable instruments or instrument assemblies may also be utilized. Thus, the procedures described herein may be utilized with manually or robotically steerable instrument systems, such as those described in the below-referenced U.S. patent application Ser. No. 11/481,433.

Exemplary embodiments of an operator control station (2), an instrument driver (16), an instrument (18) or instrument assembly (28), a robotic sheath instrument, a robotic guide instrument (18), various instruments (50), are described in detail in the following U.S. Patent Applications, and are incorporated herein by reference in their entirety:

U.S. patent application Ser. Nos. 10/923,660, filed Aug. 20, 2004; Ser. No. 10/949,032, filed Sep. 24, 2005; Ser. No. 11/073,363, filed Mar. 4, 2005; Ser. No. 11/173,812, filed Jul. 1, 2005; Ser. No. 11/176,954, filed Jul. 6, 2005; Ser. No. 11/179,007, filed Jul. 6, 2005; Ser. No. 11/202,925, filed Aug. 12, 2005; Ser. No. 11/331,576, filed Jan. 13, 2006; 60/785,001, filed Mar. 22, 2006; 60/788,176, filed Mar. 31, 2006; Ser. No. 11/418,398, filed May 3, 2006; Ser. No. 11/481,433, filed Jul. 3, 2006; Ser. No. 11/637,951, filed Dec. 11, 2006; Ser. No. 11/640,099, filed Dec. 14, 2006; 60/833,624, filed Jul. 26, 2006, and 60/835,592, filed Aug. 3, 2006.

Figure 1C:
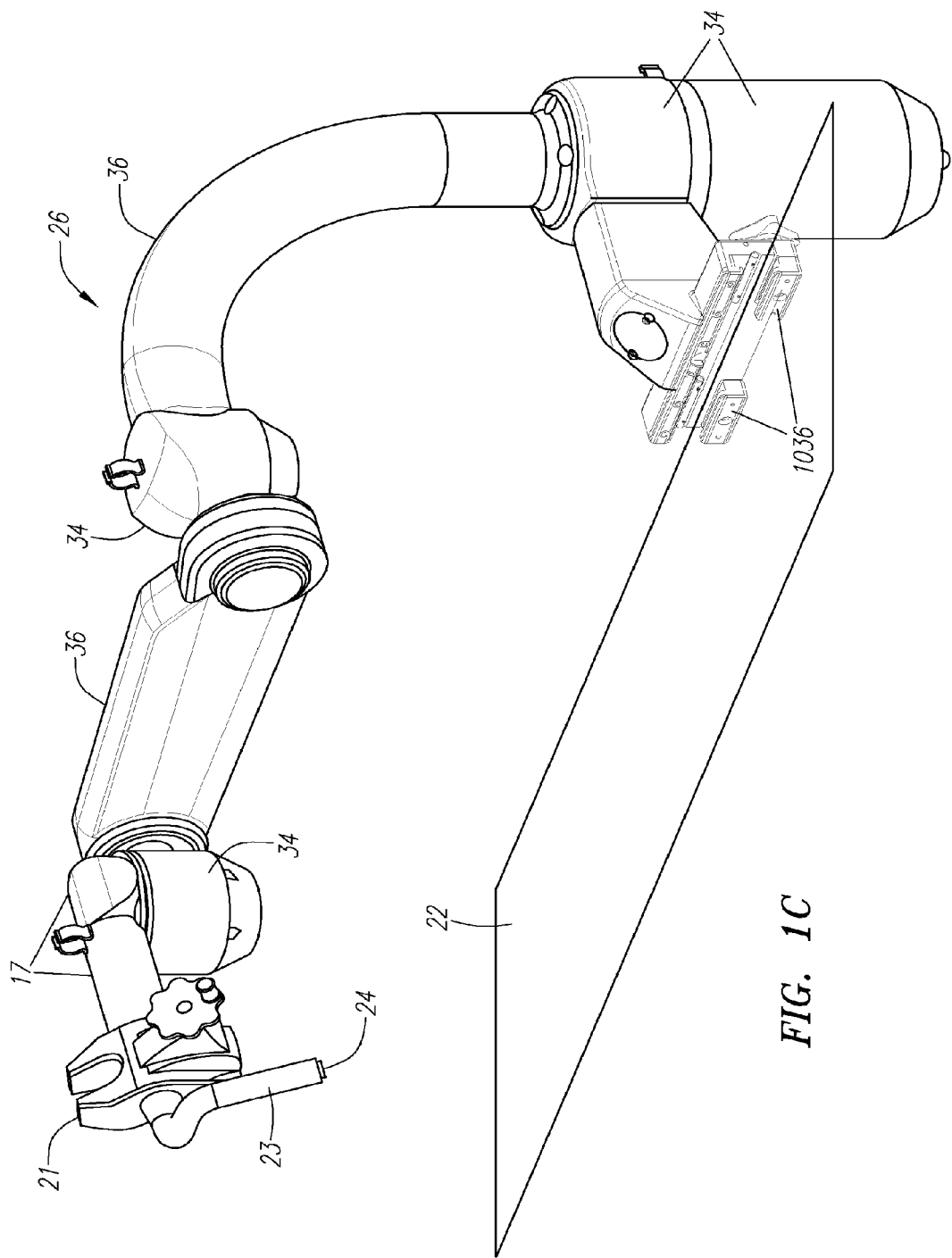
FIG. 1C illustrates one embodiment of a support assembly for supporting an instrument driver.

FIG. 1C provides a closer view of the support assembly (also referred to as a setup joint) (26) depicted in the embodiment of FIG. 1B. The support assembly (26) comprises a series of rigid links (36) coupled by electronically braked joints (34). The joints (34) allow motion of the links (36) when energized by a control system (not shown), but otherwise prevent motion of the links. The control system may be activated by a switch (e.g., a footswitch or thumbswitch), or computer interface. In another embodiment, the rigid links (36) may be coupled by mechanically lockable joints, which may be locked and unlocked manually using, for example, locking pins, screws, or clamps. The rigid links (36) preferably comprise a light but strong material, such as high-gage aluminum, shaped to withstand the stresses and strains associated with precisely maintaining a three-dimensional position of the approximately ten pound weight of a typical embodiment of the instrument driver (16) once the position of the link (36) is fixed. An instrument driver support shaft (17) is provided near the distal end of the support assembly (26), and is coupled to a pivotable instrument driver mounting interface (21) for attaching the instrument driver (16). The support assembly (26) also has an interface surface (1036) which may comprise one or more mounting clamps each generally comprising a fixed upper body portion having a mating surface, and upper and lower clamp toe portions configured for detachably coupling to a rail of an operating table (22).

Figure 2:
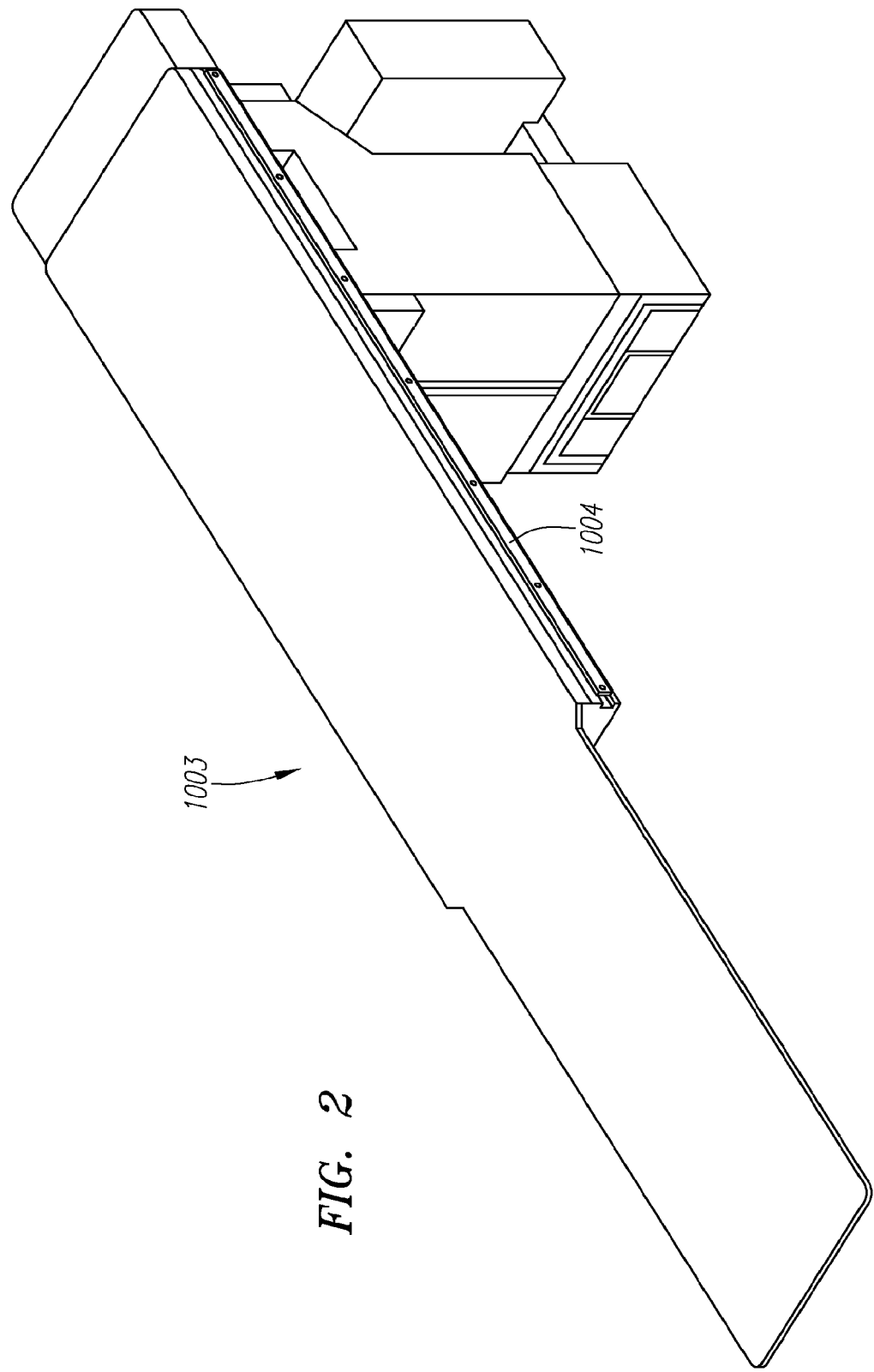
FIGS. 2-3 illustrate exemplary embodiments of operating tables.
Figure 3:
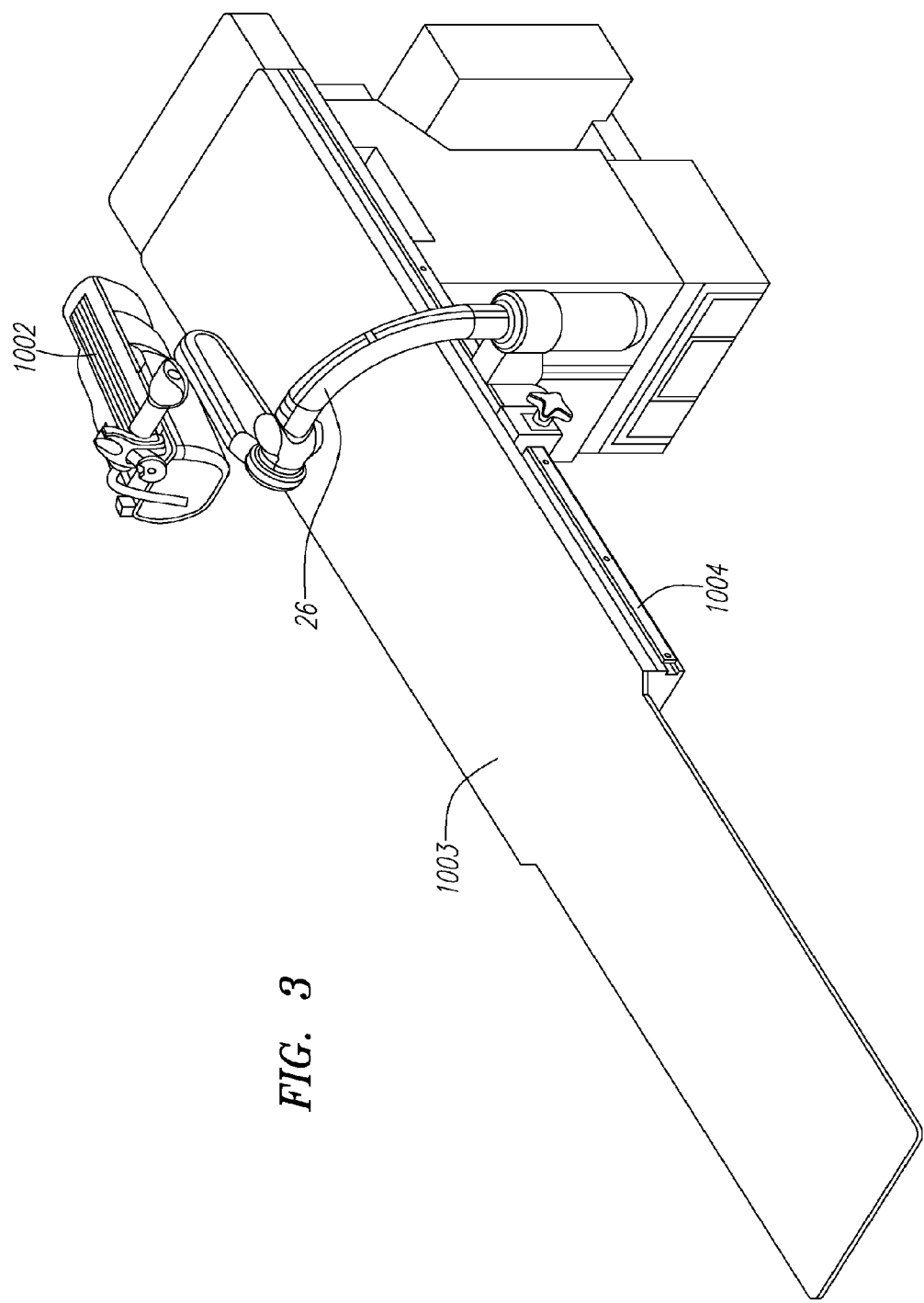
Figure 4:
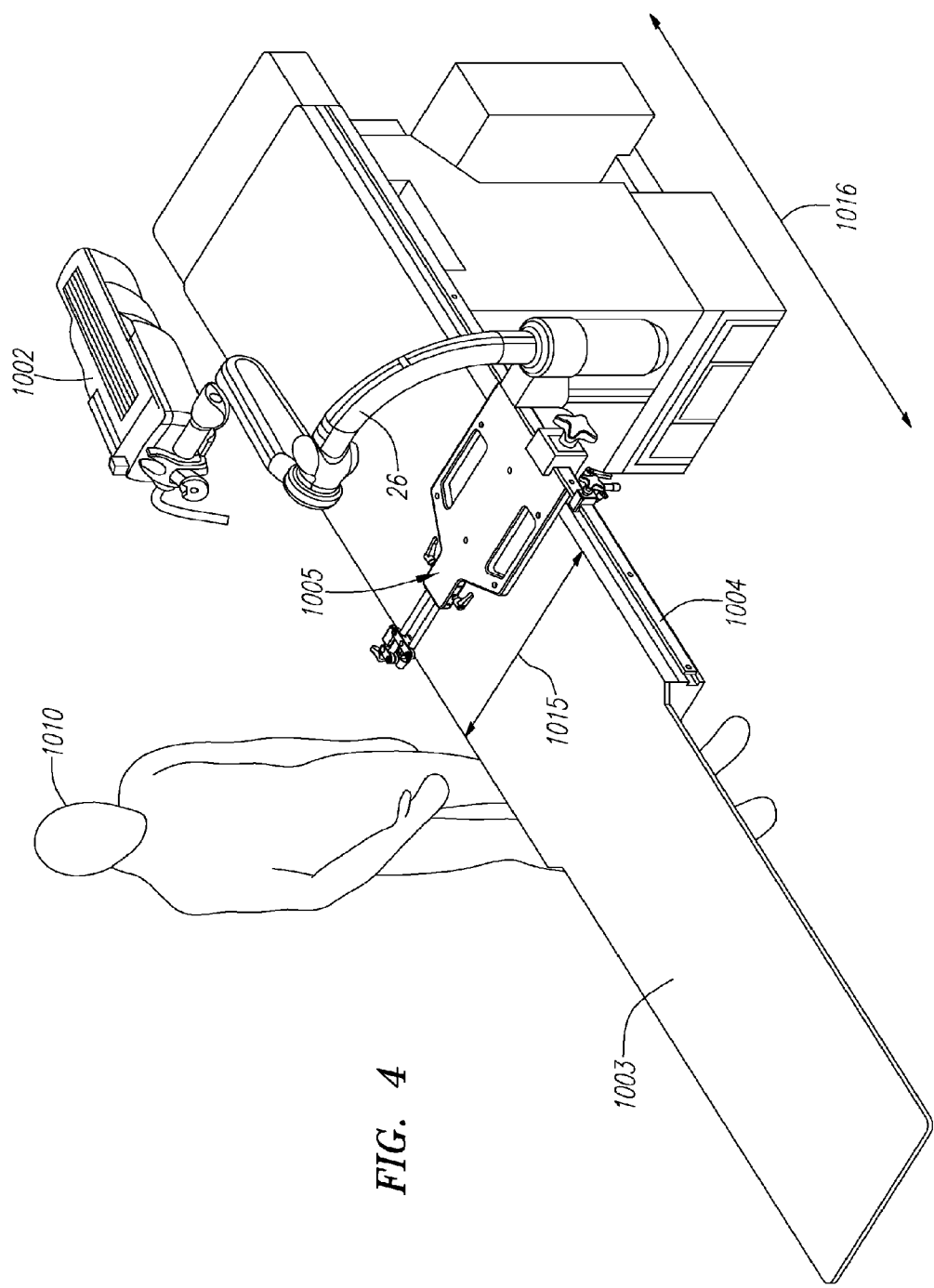
FIGS. 4-9 illustrate embodiments of a support arm adapter base plate assembly for attaching a support assembly to a operating table.
Figure 5:
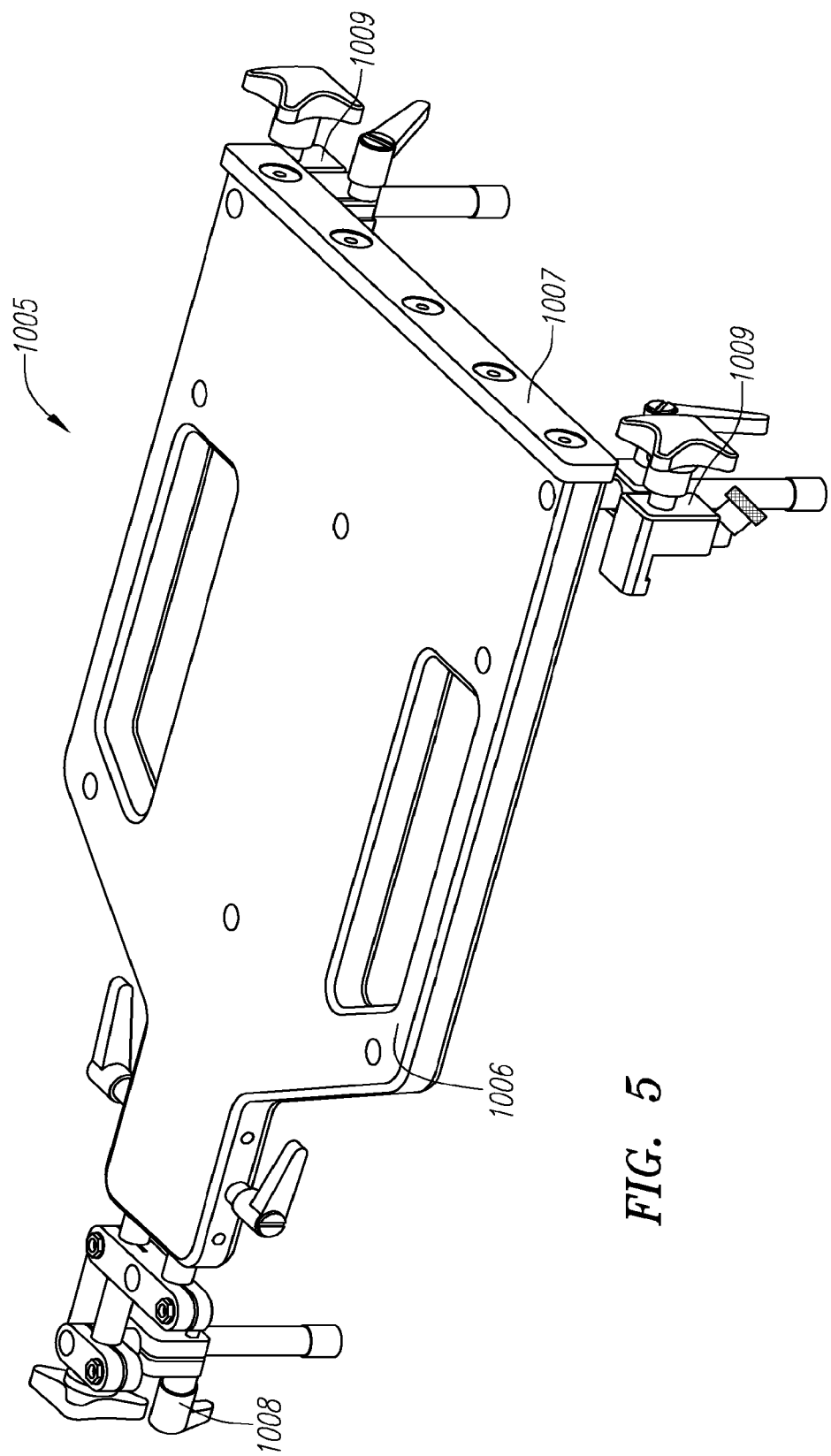
Figure 6:
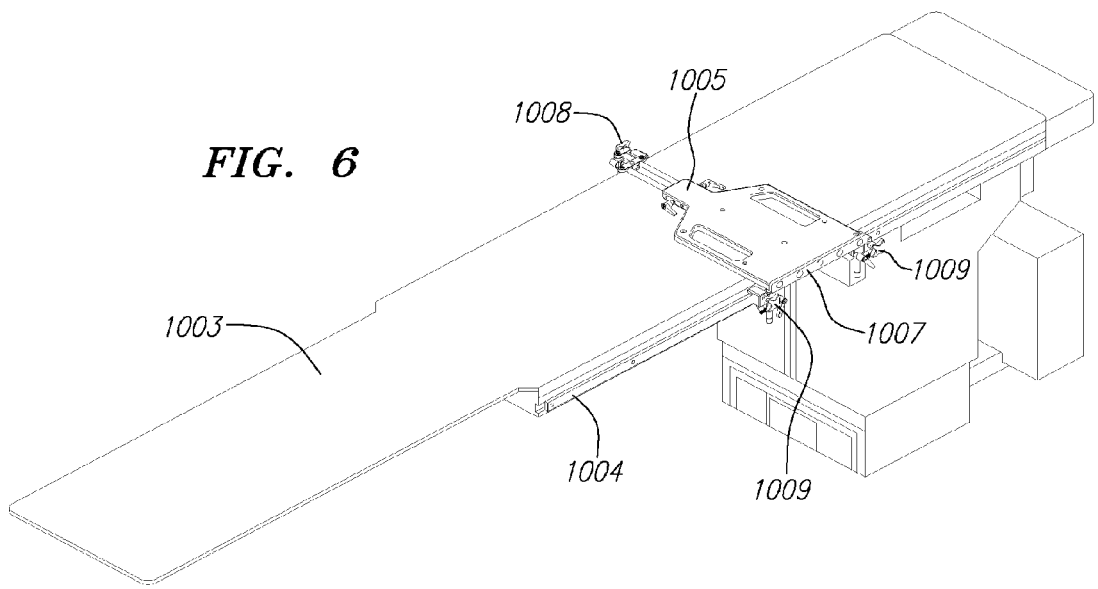
Figure 7:
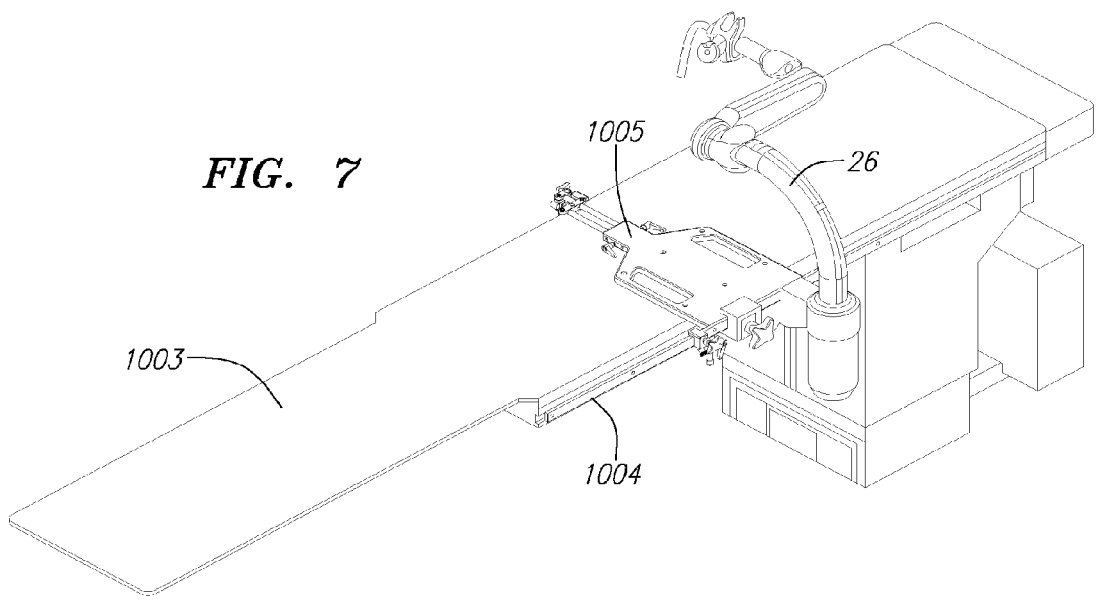
Figure 8:
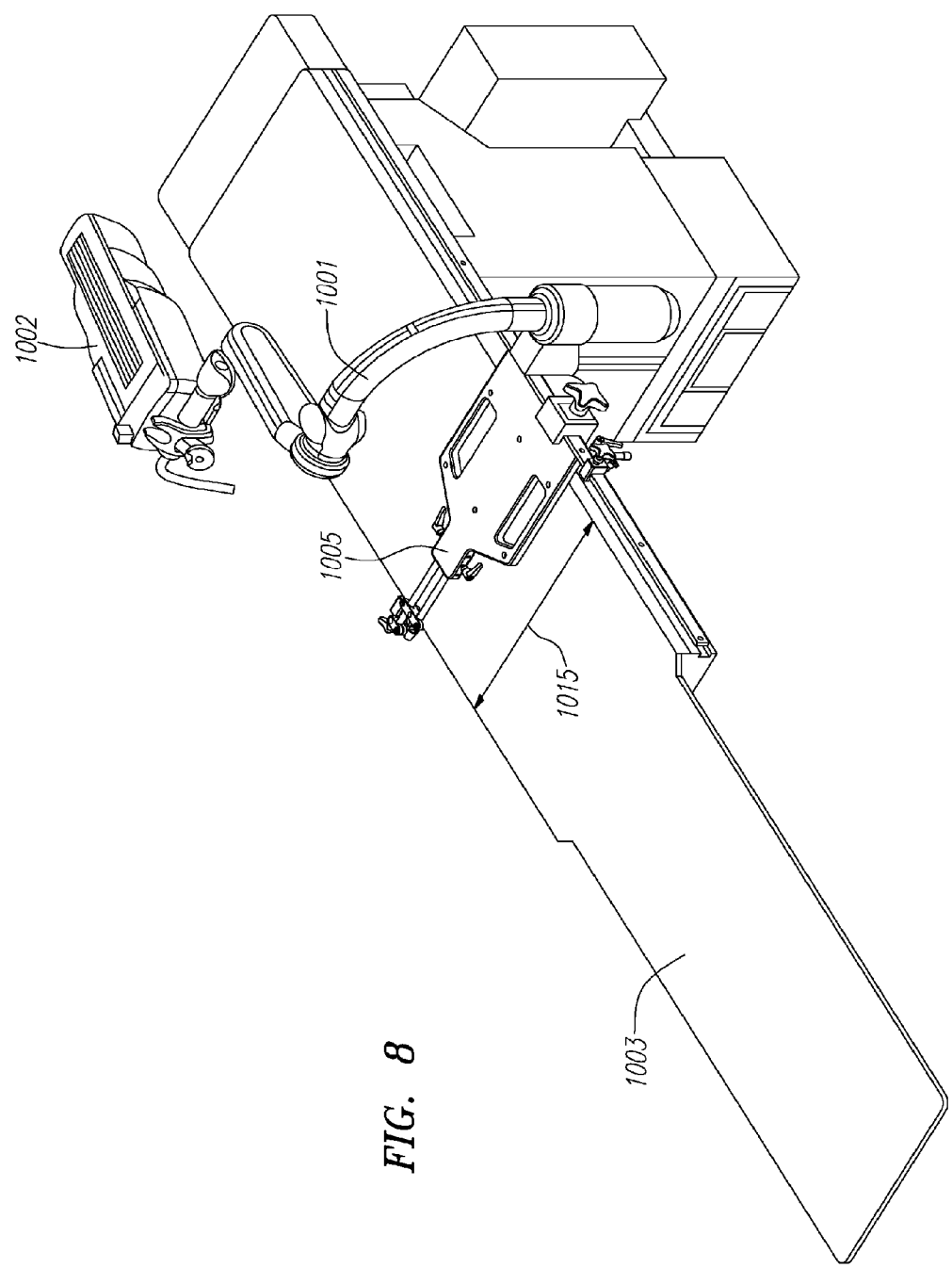

Referring now to FIGS. 2-3, an exemplary operating table (1003) is illustrated. The designs and specifications of operating tables vary widely from manufacturer to manufacturer. Operating tables (1003) not only differ between manufacturers but also between different models from the same manufacturer. Thus it is desirable to have a uniform mounting platform upon which the support assembly (26) for the above described robotic instrument system (32) may be deployed, regardless of the brand of a operating table. Furthermore, it is desirable to have a universal mounting platform that is easily adjustable and adaptable to as many different tablerails as possible. As illustrated in FIG. 1C, one embodiment of a setup joint (26) is designed to mount directly to a tablerail (1004). As a result, variations in tablerail dimensions including cross section on rails, vertical elevation, and width result in a complicated, adjustable design for the setup joint tablerail clamp (89). In some instances, the tablerails (1004) of some operating tables have shown to be weak, thus providing inadequate stiffness to support the weight of the support assembly (26) and robotic instrument assembly (1002). This may result in an unstable support assembly.

Referring to FIGS. 4-9, embodiments of a support arm adapter base plate assembly (1005) for attaching a support assembly to a operating table (1003). Adapter plate assembly (1005) mounts directly to the operating table (1003). In turn, the support assembly (26) is mounted to the adapter plate assembly (1005). In one embodiment, the adapter plate assembly (1005) comprises a large, flat main plate (1006) which lays on top of a operating table (1003). In one implementation, the assembly (1005) is designed with various adjustments to allow it to be mounted to different types of operating table. On a first edge of the adapter plate assembly (1005) is an adapter plate rail (1007) that is the same or similar to the construction of a traditional operating table rail (1004). By placing this rail (1007) on the adapter plate (1005) itself, a user may be assured that the rail on which a support assembly (26) will be mounted will have having consistent dimensions. The plate rail (1007) may be attached to the main plate (1006), such as by bolting, welding, or other suitable method, or it may be integral to the main plate (1006). Furthermore, the large, flat surface of the main plate (1006) of this embodiment provides stability by distributing the weight of the support assembly (26) and robotic instrument assembly (1002) over a relatively large area of the table, whereas a support assembly (26) mounted directly to the operating table rail (1004) causes its entire load to be placed on a limited portion of the table rail (1004). In order to mount this embodiment of an adapter plate assembly (1005), a clamp assembly (1008) and a clamp assembly (1009) are located on opposing sides of the adapter plate assembly (1005) and are configured to clamp the assembly to the operating table (1003). The clamp assembly (1008) is attached to one side of the main plate (1006) such that the first clamp assembly (1008) is located on one side of the operating table when the adapter plate assembly (1005) is installed; and the clamp assembly (1009) is attached to the opposing side of the main plate (1006) such that the clamp assembly (1009) is located on the other side of the operating table (1003) when the adapter plate assembly (1005) is installed. In this embodiment, a single clamp assembly (1008) is used on the surgeon (1010) side of the assembly while two assemblies (1009) are used on the opposite side. It is contemplated that in alternative embodiment, varying numbers of clamp assemblies (1008 and 1009) may be employed on each side of the plate assembly (1005). In this example, a single clamp assembly (1008) is used on the surgeon side of the table (1003) to minimize the amount of tableside space taken up by the adapter plate assembly (1005).

Figure 9:
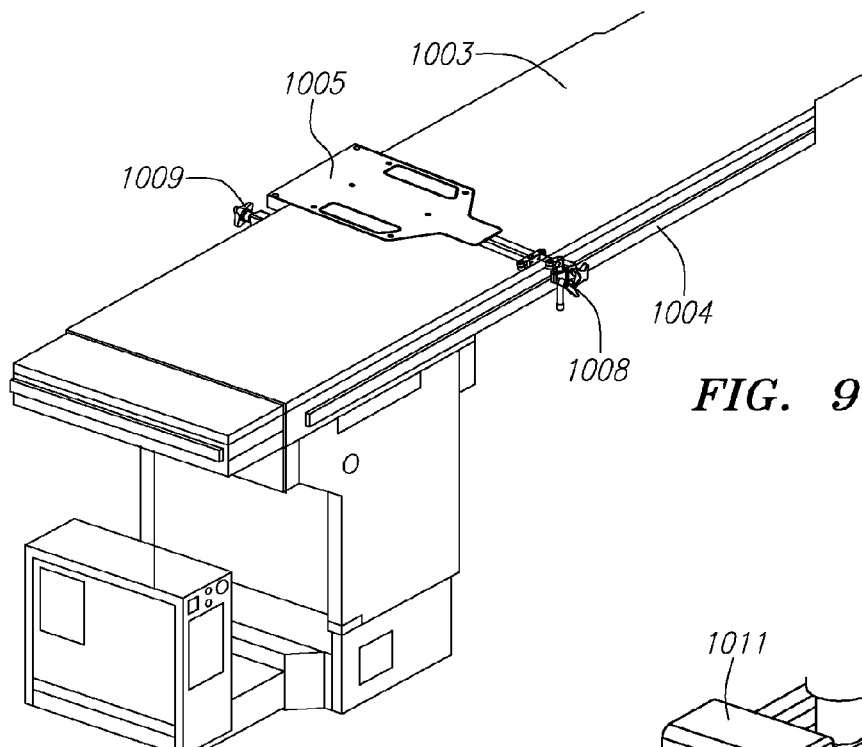

To mount the adapter plate assembly (1005), the clamp assembly (1008) on the surgeon side (1010) of the table may be removed or extended out of the way and the adapter plate assembly (1005) is placed on the top surface of the operating table (1003). The clamp assembly (1008) is repositioned on the adapter plate assembly (1005) and the clamp assemblies (1008 and 1009) on both the surgeon side 1010 and the opposing side of the table are tightened onto the operating table rails (1004). The support assembly (26) may then be mounted to the adapter plate rail (1007) and placed over the entire adapter plate assembly (1005). FIG. 9 illustrates a operating table (1003) with adapter plate assembly (1005) installed from the surgeon (1010) side of the table (1003).

Figure 9A:
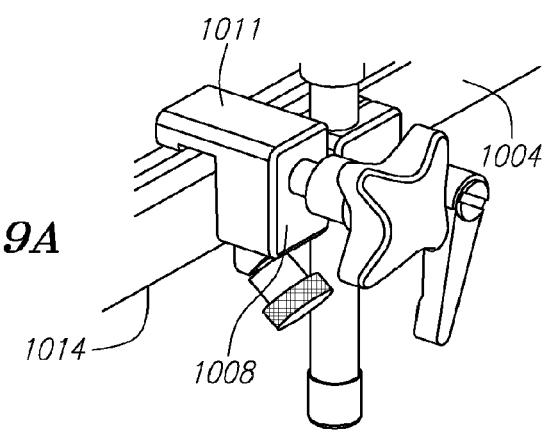
Figure 10:
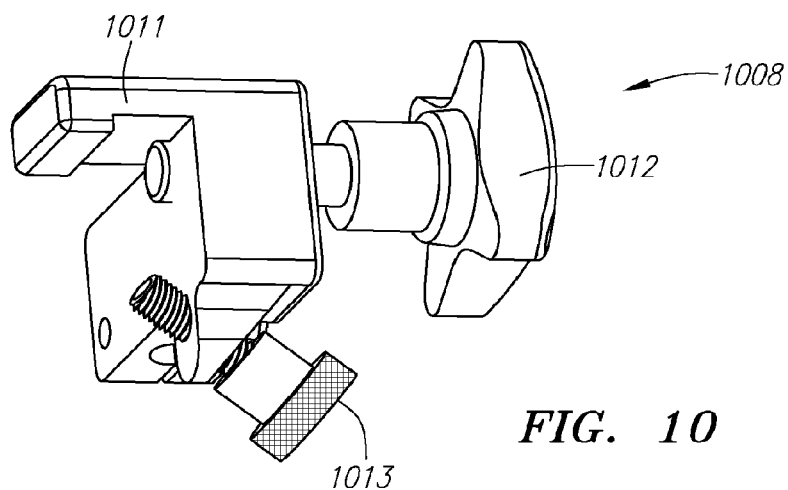
Figure 20:
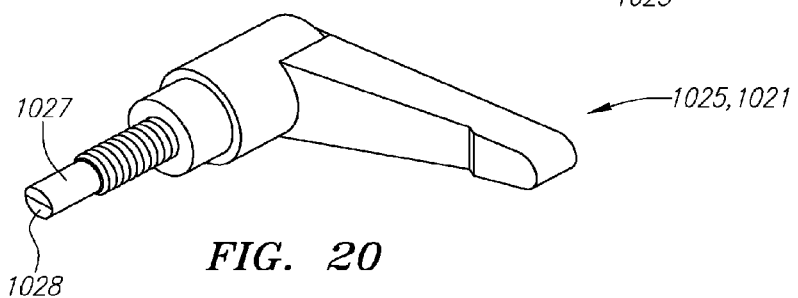
FIGS. 20-21 illustrate different views of one embodiment of an adjustment knob.

Referring to FIGS. 9A and 10, one embodiment of a clamp assembly (1008/1009) is illustrated. FIG. 9A illustrates a first perspective view of a clamp assembly (1008) mounted to a table rail (1004). FIG. 20 illustrates another perspective view of a clamp assembly (1008). In one embodiment, the clamp assemblies (1008/1009) on both sides of the adapter plate assembly (1005) are identical in design. Each clamp assembly (1008/1009) comprises an upside down L-shaped metal clamp (1011) which hooks around the top of the table rail (1004). The clamp assembly (1008) fits on top of the table rail (1004) and a large knob (1012) threaded through clamp (1011) may be adjusted to tighten directly against the table rail (1004), thus pulling the hook of the clamp (1011) against the table rail (1004) and locking the clamp (1011) in place. Another knob (1013) is threaded through the clamp (1011) directly below the large knob (1012) but is threaded through at an upward angle. This angled knob (1013) catches the underside (1014) of the table rail (1004). The knob (1013) serves as a secondary locking mechanism to the main knob (1012) and also prevents any twisting due to an unexpected large moment about the operating table.

Figure 11:
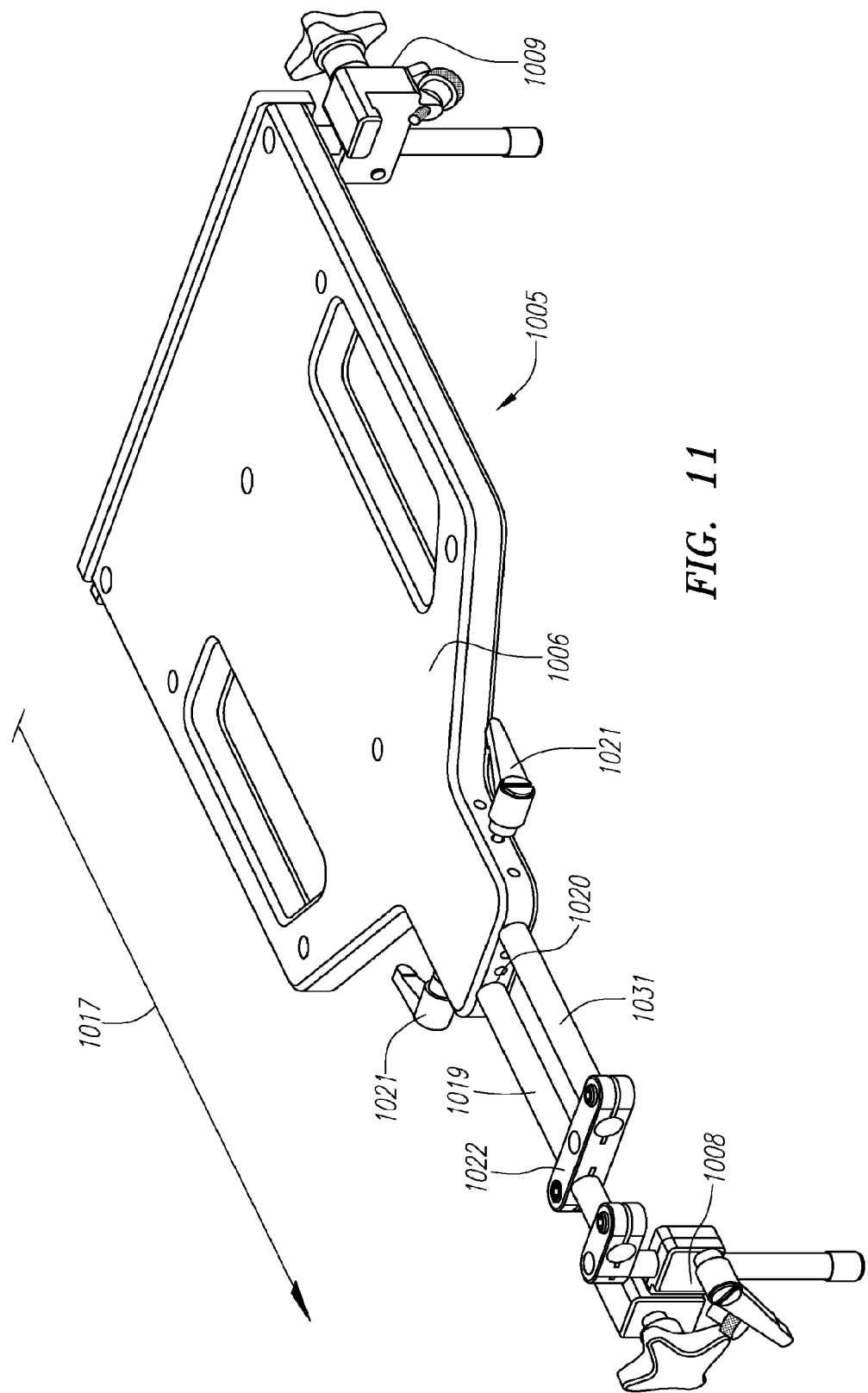
FIG. 11 illustrates a perspective view of one embodiment of an adapter plate assembly.
Figure 12:
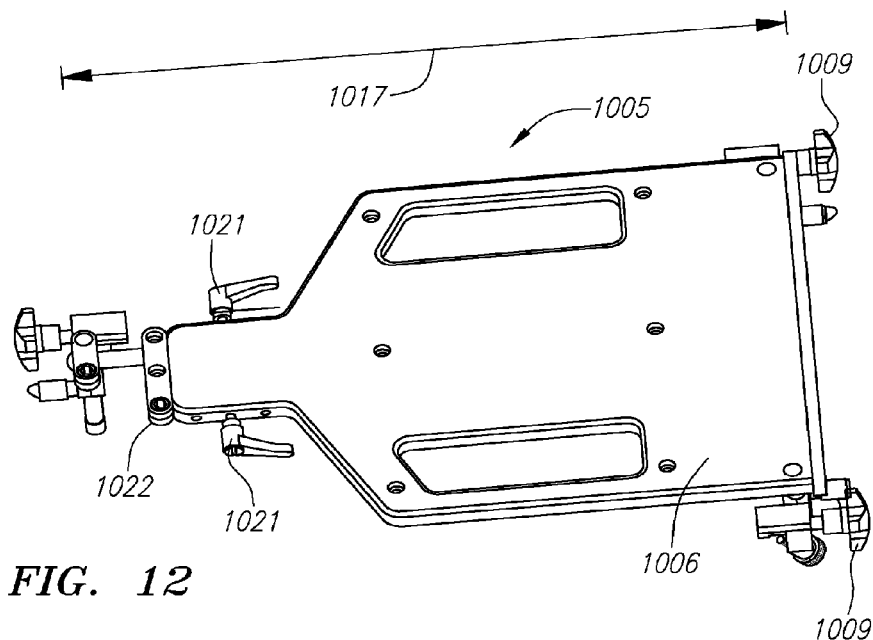
FIG. 12 illustrates the adapter plate assembly of FIG. 11 in a first, retracted configuration.
Figure 13:
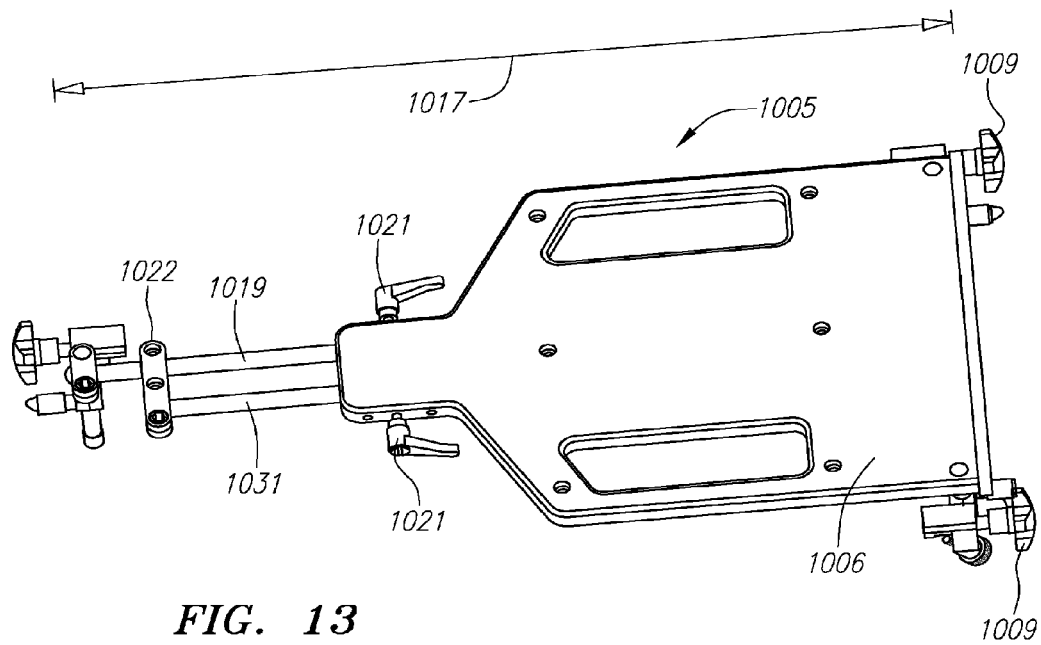
FIG. 13 illustrates the adapter plate assembly of FIG. 11 in a second, extended configuration.

FIGS. 11-13 illustrate a first manner of adjustment of an embodiment of the adapter plate assembly (1005) which allows the plate assembly (1005) to be installed on operating tables (1003) that have different widths. FIGS. 11 and 12 illustrate another perspective view of one embodiment of the adapter plate assembly (1005) in a first, retracted configuration. FIG. 13 illustrates the adapter plate assembly in a second, extended configuration. The first adjustable element of the adapter plate assembly (1005) concerns the width (1017) of the adapter plate assembly (1005). In this embodiment, the plate assembly (1005) is adjustable to fit the width (1015) of the operating table (1003) (see FIG. 8). In order to accomplish this, the surgeon side clamp assembly (1008) is mounted on two adjustable rods (1019/1031) that fit in two holes (1020) that run parallel to the width (1017) of the adapter main plate (1006) on one end, and are coupled to a split clamp (1022) on the other end. The rods (1019/1031) are held in place by two set knobs (1021) threaded into the main plate (1006). By loosening both set knobs (1021), the rods (1019/1031) are able to slide in and out, thereby essentially increasing and decreasing the effective width of the adapter plate (1005). When the desired width is achieved, the set knobs (1021) are tightened and the rods (1019/1031) are locked into place. Two adjustable rods (1019 and 1031) are used instead of a single rod to prevent the surgeon side clamp (1008) from rotating about the rod (1019) axis. Having two rods also allows for redundancy so that if one rod (1019 or 1031) breaks or if one knob (1021) fails, the other remains to preserve the functionality of the system. Similarly, the one or more clamp assemblies (1009) may also be adjustable to adjust the width of the plate assembly (1005).

Figure 14:
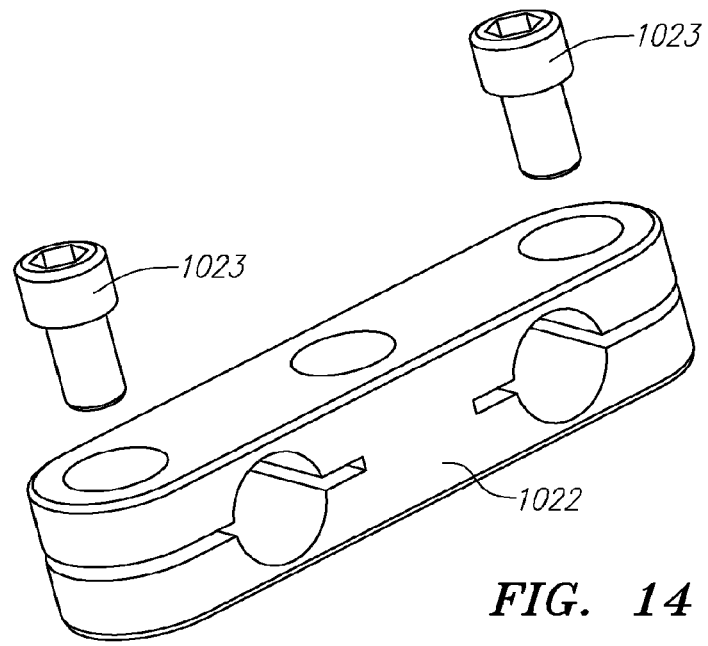
FIGS. 14-15 illustrate one embodiment of a split clamp and associated rods.
Figure 15:
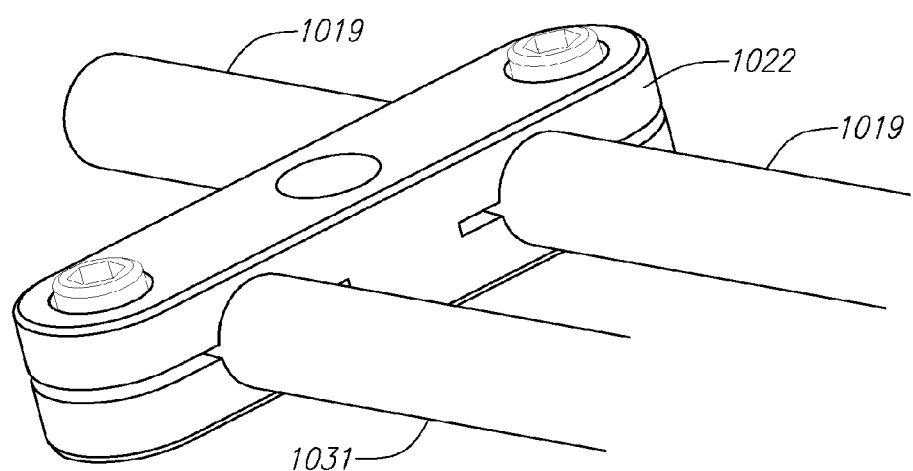

FIGS. 14-15 illustrate the split clamp (1022) and associated rods (1019/1031). The adjustable rods (1019/1031) are held at their distal ends with a split clamp (1022). The split clamp (1022) is tightened with screws (1023) that sandwich and tighten the split clamp (1022) around the rods (1019 and 1031). One of the rods (1019) extends beyond the main split clamp (1022) to the distal end of the assembly where it couples to the clamp assembly (1008). In one embodiment, the adjustable rods (1019/1031) are configured such that the adapter plate assembly (1005) may extend its width (1017) to about 36 inches, or more. In a case where a table may be wider than 36 inches, the rods (1019/1031) may be replaced with longer length rods.

FIG. 16 illustrates an enlarged perspective view of the portion of one embodiment of a plate assembly (1005) near the surgeon side. FIGS. 17-18 illustrate an enlarged perspective view o the clamp assembly (1008) of one embodiment. In this implementation, the clamp assemblies (1008/1009) for a single plate assembly are identical. A clamp assembly is now described. Each clamp assembly (1008/1009) also allows for a vertical adjustment. Because the distance between the top surface of the table (1003) and the table rail (1004) can vary as much as 3-4 inches from table-to-table, a height adjustment on the clamp assembly (1005) is needed in order to be able to mount the adapter plate clamps (1008/1009) to different types of tables. The vertical adjustment is achieved by providing the clamp component (1011) with a split clamp (1023) that can slide up and down on a vertical rod (1024). The split clamp (1023) in its relaxed state has an inner diameter that is larger than the outer diameter of the vertical rod (1024). A threaded set knob (1025) passes through a through-hole in one side of the clamp (1023) and threads into the other side so that when the knob is tightened, the split clamp (1023) closes, decreasing its inner diameter and locking it onto the vertical rod (1024). The maximum vertical adjustment is obtained by sliding the clamp assembly (1008/1009) to the bottom of the vertical rod (1024). If it becomes necessary to extend the vertical maximum for extremely thick tablerails, the vertical rods (1024) could be swapped out for longer rods. Although currently the vertical rods (1024) are pressed and pinned into the clamp component (1011), an alternative embodiment may include swappable rods. In another embodiment, the interface between the rod (1024) and the small split clamp (1032) may be threaded together with a locking nut to lock the rod in place.

Figure 19:
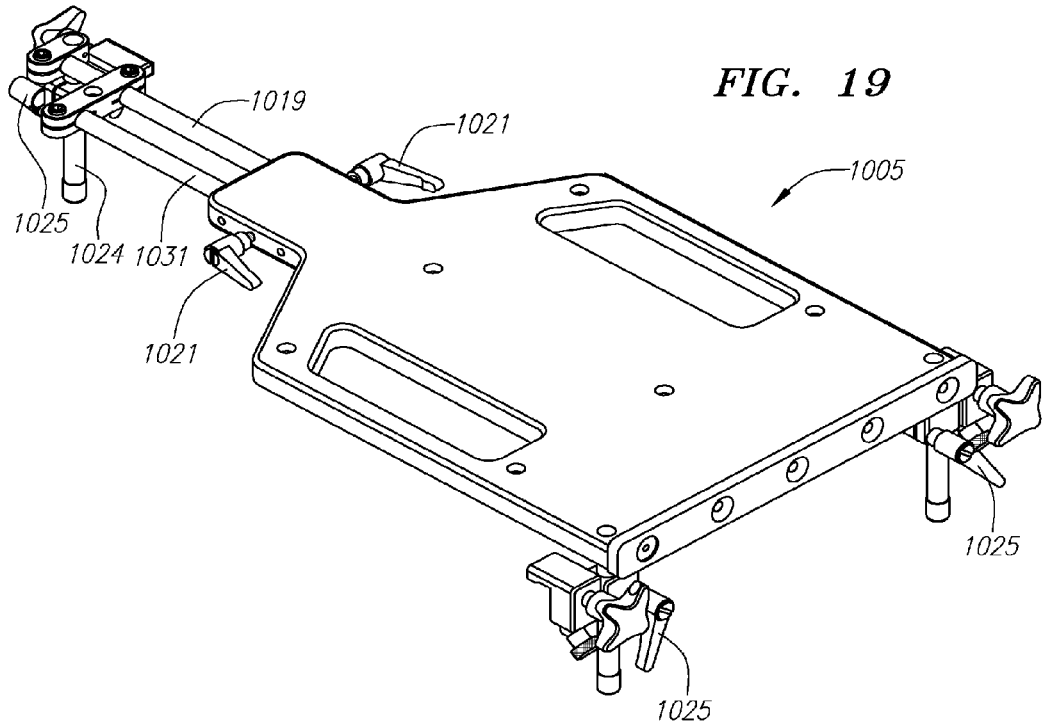
FIG. 19 illustrates another perspective view of one embodiment of the adapter plate assembly.
Figure 21:
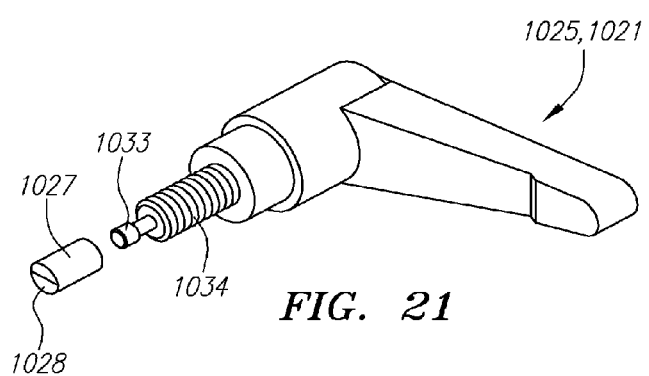

FIG. 19 illustrates another perspective view of one embodiment of the plate assembly (1005). FIGS. 20-21 illustrate different views of one embodiment of the adjustment knob (1021/1025). The set knobs (1021) are used for adjustment of the clamp assemblies (1008 and 1009) and the set knobs (1025) are used for adjustment of the adapter plate width adjustment rods (1019/1031). The set knobs (1021/1025) may be a ratchet type knob for safety wherein the knob does not engage its threads by simply spinning the knob. In order to engage the threads, the knob has to be forced down into the threads along its spinning axis while spinning the knob. A locking element (1027) is threaded on the distal end of the adjustment knob (1021 and 1025). The locking element (1027) comprises a groove (1028) that matches the adjustable rods (1019/1031) and vertical rod (1024) such that the groove can press up against the respective rod and lock it into place. The locking element (1027) is threaded onto the knob (1021/1025) to capture it in the assembly so when the rod (1019/1031/1024) is removed from the assembly the locking element (1027) does not fall out. In one embodiment, the threads on the distal portion (1033) of the adjustment knob are reversed from the threads on the proximal end (1034), i.e. left handed threads to prevent the locking element (1027) from loosening when the adjustment knob (1021/1025) is tightened into place to lock the adjustment rod (1019/1031/1024).

Figure 22:
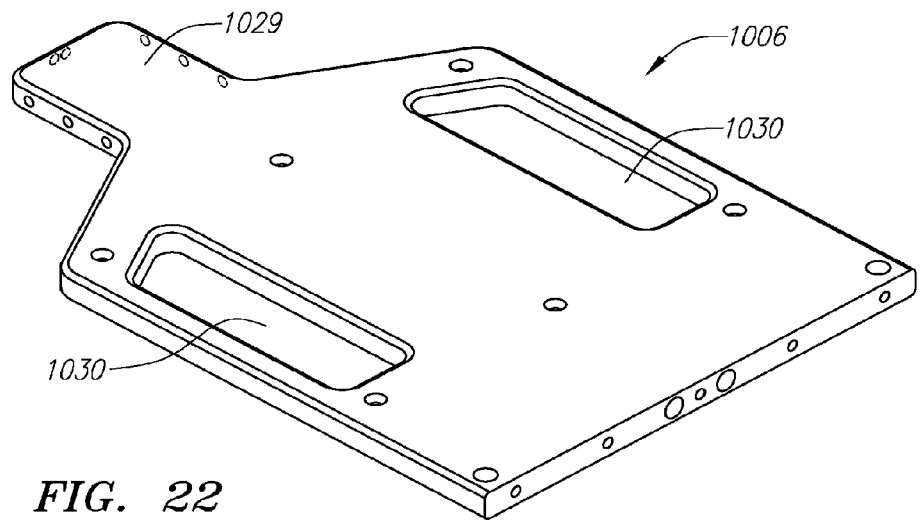
FIGS. 22-23 illustrate different views of one embodiment of the main plate of the adapter plate assembly.
Figure 23:
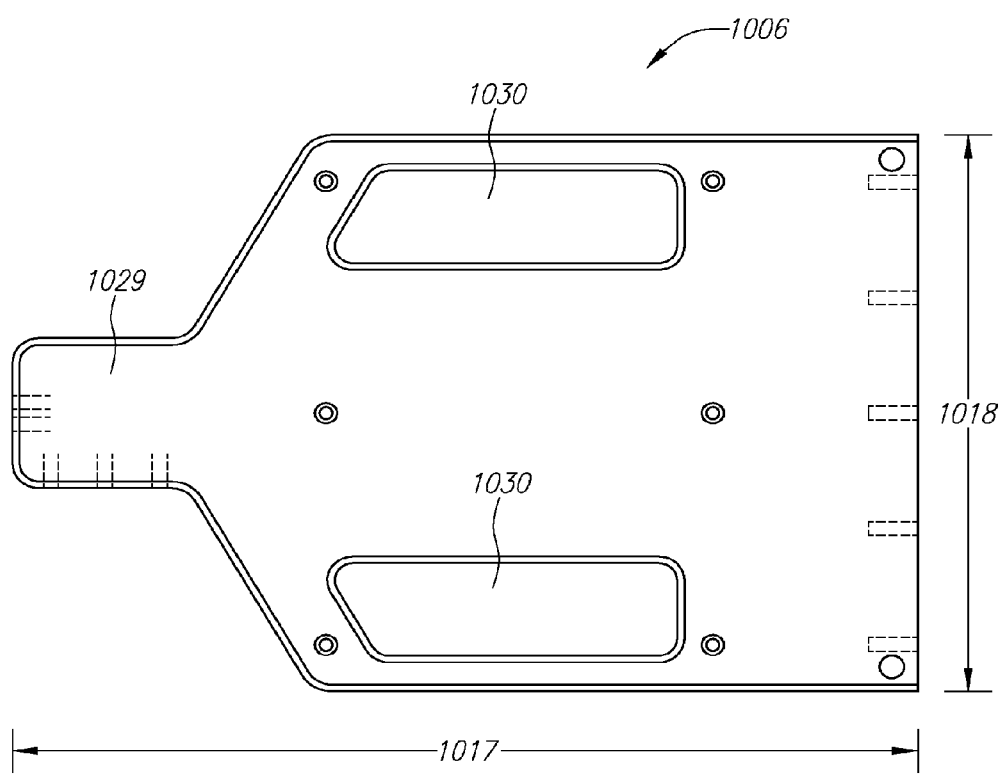

FIGS. 22-23 illustrate different views of one embodiment of the main plate (1006) of the adapter assembly (1005). From a top view, the adapter main plate (1006) is shaped like a rectangle that tapers off to create a neck like portion (1029). The main plate (1006) is shaped so that its width dimension in the neck like portion (1029) is smaller on the surgeon (1010) side of the table and has a much wider width (1018) on the opposite side of the table. The wide length (1018) on the opposite side of the table is intended to increase stability and safety. First, the wide edge (1018) allows for two clamp assemblies (1009) that can be spaced further apart. Second, increasing the overall size of the plate gives the plate (1006) some size and weight to safely hold the support arm assembly (26) and instrument driver (1002) in place even if the clamp assemblies (1008/1009) are mistakenly loosened or insufficiently tightened. The smaller width neck (1029) of the main plate (1006) in this example is intended to reduce the amount of table rail (1004) space used on the surgeon side of the table (1003). In some instances, a operating table (1003) may have several pendants mounted to its table rail (1004) on the surgeon side (1010) for flouroscopy, display screens, ablation tools, etc. Thus the necking (1029) in one embodiment of a plate reduces the need of the table rail (1004) space to approximately 3 inches. In alternative embodiments, this necking may be reduced or eliminated such that the surgeon side of the plate may be resized to wider dimensions as desired. Additionally, one of the adjustable rods (1019) is extended to hold the clamp assembly (1008). The rod (1019) is extended to be able to achieve the minimal three inch tablerail (1004) space taken by the single clamp assembly (1008). A smaller split clamp (1032) holds the distal end of the fixed rod (1019) and functions identically to the split clamp (1022). For one implementation, the thickness of the main plate (1006) is chosen to be ¾" inch. Because the plate is installed underneath a patient's feet, it is important that the thickness of the plate does not elevate the feet significantly. With more clinical data, the thickness of the main plate (1006) can be increased. When the adjustable rods (1019/1031) are pulled out to extend the width of the plate assembly (1005), the extended portion (1035) (see FIG. 24) of the assembly does not include the thickness of the main plate (1006). Should a patient lying on the surgical table have one foot elevated by the main plate a greater amount than the other foot, a block can be placed over the rods to correct for this height discrepancy. The main plate (1006) also includes a pair of cut-outs (1030) which can be used as handles for handling the plate assembly (1005) and also to reduce the overall weight of the main plate (1006).

Figure 24:
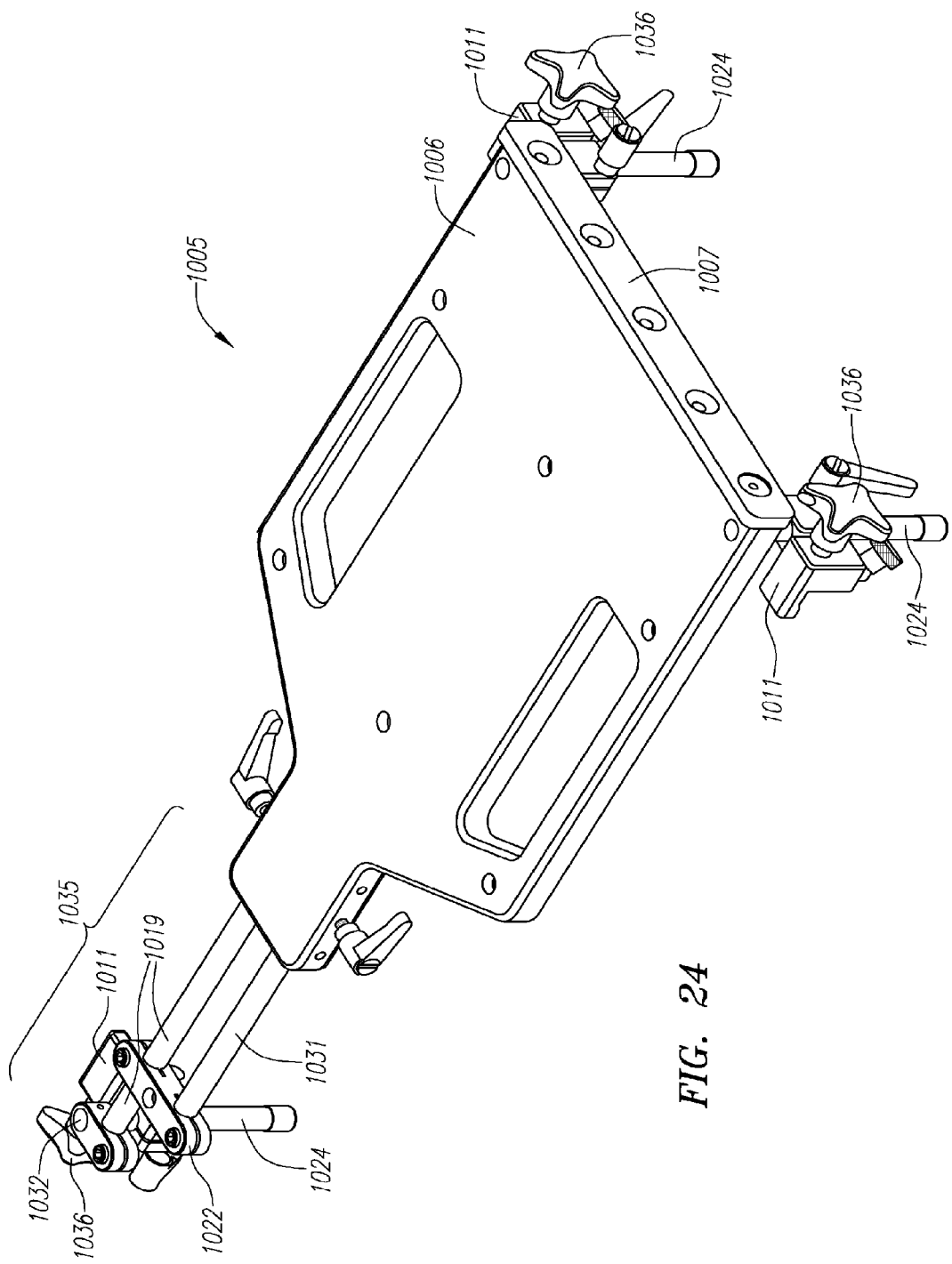
FIG. 24 illustrates yet another view of the adapter plate assembly of one embodiment.

FIG. 24 illustrates yet another view of one embodiment of the adapter plate assembly (1005). In one implementation, the main plate (1006) is aluminum and the adapter plate rail (1007) is steel. In alternative embodiments, other types of materials, metallic or non-metallic, may be used to construct the various elements of the adapter plate assembly (1005). The adjustment rods (1019/1031/1024) (both for width and vertical adjustments) of this embodiment may be constructed of steel. The split clamps (1022/1032) holding the rod (1024) and the adjustable rods (1019/1031) may also fabricated from steel in this embodiment. In other embodiments non-metallic materials such as carbon fibers may be used instead of aluminum and steel. In alternative embodiments, an assembly with a minimal amount of metal may be desirable to reduce interference with any imaging modalities that may be used during a surgical procedure.

Figure 25:
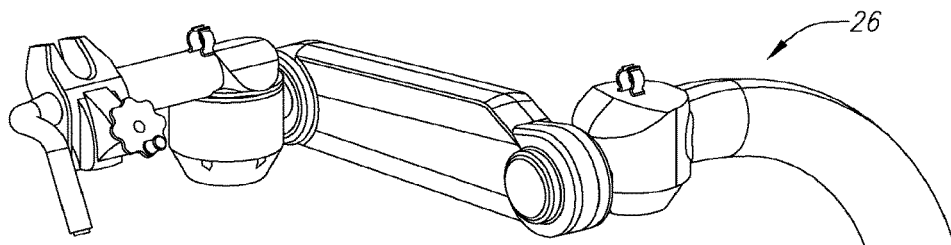
FIG. 25 illustrates one embodiment of a support assembly.
Figure 26:
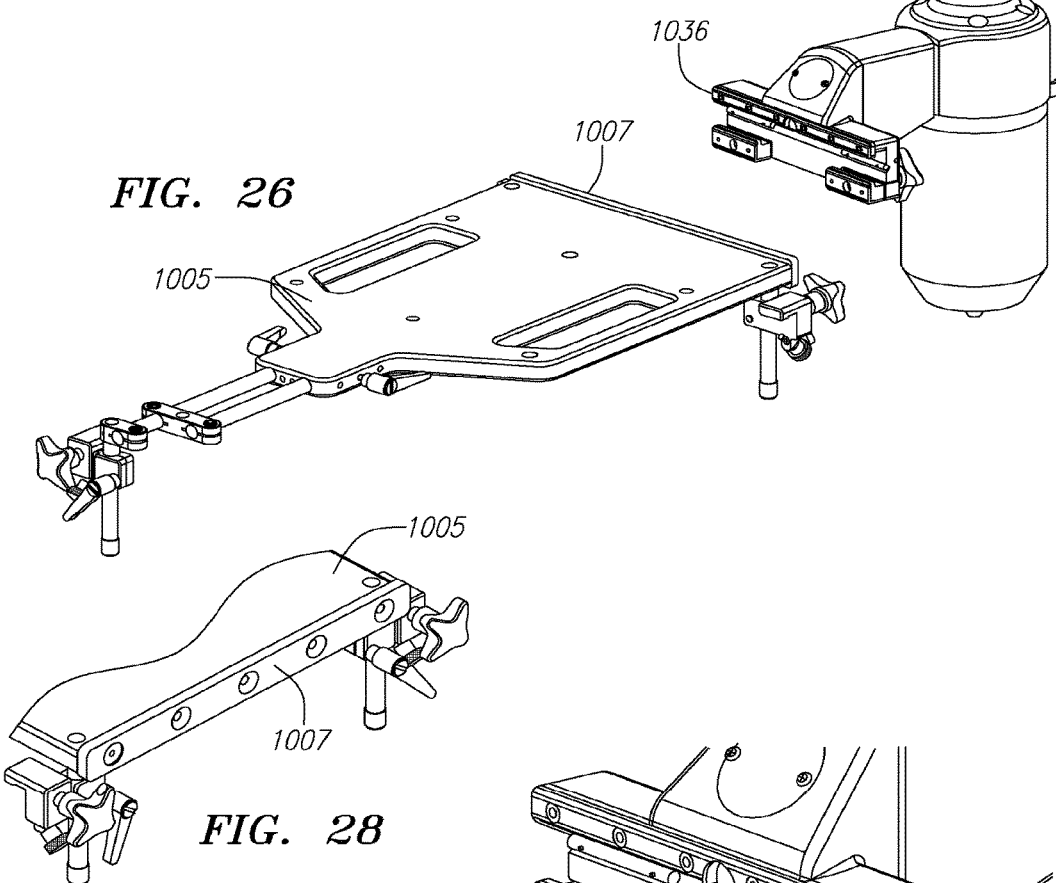
FIG. 26 illustrates one embodiment of an adapter plate assembly oriented to receive the support assembly of FIG. 25.
Figure 28:
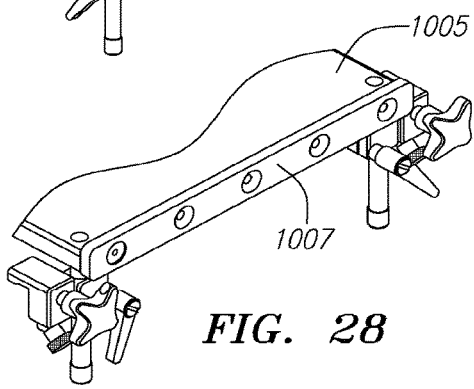
FIG. 28 illustrates an enlarged view of the adapter plate rail for the adapter plate assembly of FIG. 26.
Figure 27:
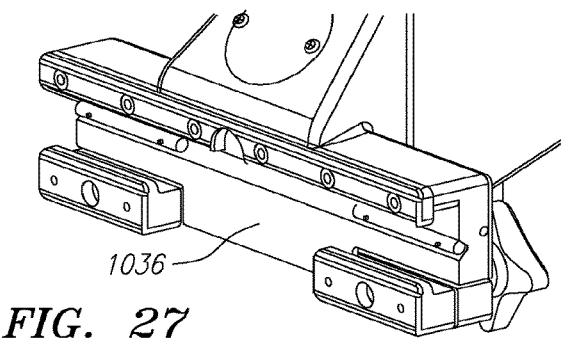
FIG. 27 illustrates an enlarged view of the support assembly interface for the support assembly of FIG. 25.

FIG. 25 illustrates the support assembly (26) of one embodiment. FIG. 26 illustrates one embodiment of an adapter plate assembly (1005) oriented to receive the support assembly (26) of FIG. 25. FIG. 27 illustrates an enlarged view of the support assembly interface surface (1036) for the support assembly (26) of FIG. 25. FIG. 28 illustrates a close up view of the adapter plate rail (1007) for the adapter plate assembly (1005) of FIG. 26. In order to prevent a user from accidentally installing the setup joint (26) directly onto the operating table rail (1004) instead of first installing the adapter plate assembly (1005) and then installing onto the adapter plate rail (1007), the interface between the adapter plate rail (1007) and the support assembly interface (1036) may be specifically keyed. For example, the support assembly interface (1036) can be angled or keyed to match a mirror image shaped surface on the adapter plate rail (1007), so that the setup joint (26) can only be mounted to the adapter plate assembly (1005). Another advantage of this adapter plate platform apparatus is the ability to be able to mount a support assembly (26) anywhere on the operating table, whether it be surgeon side, far side, center of table, etc.

Another embodiment for this adapter plate assembly (1005) is designed to hold multiple support assemblies (26) and multiple instrument drivers (16). By altering the main plate (1006), another rail (1007) may be added to the other side of the table. Furthermore, an additional rail could be added to mount a support assembly (26) that extends from between the patients legs, etc. If desired, a secondary rail can be added on the same side of the adapter plate assembly (1005) that extends further from original rail (1007) such that a pair of support assemblies (26) may be mounted on the same side of the table; or the rail (1007) can be lengthened such that it can accommodate two or more support assemblies (26). Furthermore, the adapter plate assembly (1005) may be configured such that the main plate (1006) is place underneath the operating table (1003), instead of on top of the operating table (1003).

While multiple embodiments and variations of the many aspects of the invention have been disclosed and described herein, such disclosure is provided for purposes of illustration only. Many combinations and permutations of the disclosed system are useful in minimally invasive surgery, and the system is configured to be flexible, and it should be understood that the invention generally, as well as the specific embodiments described herein, are not limited to the particular forms or methods disclosed, but also cover all modifications, equivalents and alternatives falling within the scope of the appended claims.

What is claimed is:

1. A mounting assembly disposed on a patient table, the mounting assembly comprising:
   a load distributing plate disposed on and supported by a top surface of the patient table, the load distributing plate having a first edge;
   a load distributing rail positioned along the first edge; and
   an elongate support assembly comprising:
      a first end;
      a second end;
      a mounting interface at the first end, comprising an elongate mating surface that is complementary in shape to a length of the load distributing rail, encloses the load distributing rail, and is removably engageable with the load distributing rail along the length; and
      a load secured to the second end,
   wherein engagement between the mounting interface and the load distributing rail securely mounts the elongate support assembly to the load distributing plate along the load distributing rail, and
   wherein the support assembly is cantilevered over a portion of the load distributing plate, such that the load secured to the second end of the support assembly is supported by the load distributing plate and suspended over the patient table.

2. The mounting assembly of claim 1, wherein the elongate support assembly comprises an arcuate member.

3. The mounting assembly of claim 1, wherein the elongate support assembly comprises a plurality of links coupled by a plurality of joints.

4. The mounting assembly of claim 1, further comprising a first clamp detachably securing the first edge of the load distributing plate to a first table edge of the patient table.

5. The mounting assembly of claim 4, further comprising a second clamp detachably securing a second edge of the load distributing plate to a second table edge of the patient table.

6. The mounting assembly of claim 5, wherein a distance between the first and second clamps is adjustable, thereby allowing the first and second clamps to detachably secure the mounting assembly to patient tables having first and second table edges with different distances therebetween.

7. The mounting assembly of claim 4, wherein the patient table comprises a table rail secured to the first table edge, wherein the first clamp detachably secures the first edge of the load distributing plate to the table rail.

8. The mounting assembly of claim 7, wherein the first clamp comprises a top component and a bottom component, and wherein a vertical distance between the top component and the bottom component is adjustable, thereby allowing the first clamp to detachably secure the mounting assembly to patient tables having different distances between respective top surfaces of the patient tables and table rails.

9. The mounting assembly of claim 1, wherein the load secured to the second end of the support assembly comprises a robotic medical device driver.

10. The mounting assembly of claim 1, wherein the load distributing rail extends horizontally along the first edge of the load distributing plate, and the elongate mating surface of the mounting interface extends horizontally parallel to the load distributing rail.

11. The mounting assembly of claim 1, wherein the elongate mating surface of the mounting interface is angled or keyed to uniquely complement and engage with the load distributing rail.

12. A mounting assembly disposed on a patient table, the mounting assembly comprising:
   a load distributing plate disposed on and supported by a top surface of the patient table, the load distributing plate having a first edge and a second edge;
   a first load distributing rail positioned along the first edge;
   a second load distributing rail positioned along the second edge; and
   first and second elongate support assemblies having respective first and second ends with a respective mounting interface at each of the first ends and a respective load at each of the second ends, wherein each respective mounting interface comprises an elongate mating surface that is complementary in shape to a length of the respective load distributing rails, encloses the load distributing rails, and is removably engageable with the respective load distributing rails along the length, wherein engagement between each mounting interface and the respective first and second load distributing rails securely mounts the first and second support assemblies to the load distributing plate along the first and second load distributing rails, respectively, and wherein each of the first and second support assemblies is cantilevered over respective portions of the load distributing plate, such that the respective loads secured to the second ends of the respective first and second support assemblies are supported by the load distributing plate and suspended over the patient table.

13. The mounting assembly of claim 12, wherein each of the first and second elongate support assemblies comprises an arcuate member.

14. The mounting assembly of claim 12, wherein each of the first and second elongate support assemblies comprises a plurality of links coupled by a plurality of joints.

15. The mounting assembly of claim 12, further comprising a first clamp detachably securing the first edge of the load distributing plate to a first table edge of the patient table.

16. The mounting assembly of claim 15, further comprising a second clamp detachably securing the second edge of the load distributing plate to a second table edge of the patient table.

17. The mounting assembly table of claim 16, wherein a distance between the first and second clamps is adjustable, thereby allowing the first and second clamps to detachably secure the mounting assembly to patient tables having first and second table edges with different distances therebetween.

18. The mounting assembly of claim 12, wherein the load secured to the second end of the first support assembly comprises a robotic medical device driver.

19. A mounting assembly disposed on a patient table, the mounting assembly comprising:

a load distributing plate disposed on and supported by a top surface of the patient table, the load distributing plate having an edge;

a load distributing rail positioned along the edge; and first and second elongate support assemblies having respective first and second ends with a respective mounting interface at each of the first ends and a respective load at each of the second ends, wherein each mounting interface comprises an elongate mating surface that is complementary in shape to a length of the load distributing rail, encloses the load distributing rail, and is removably engageable with the load distributing rail along the length, wherein engagement between each mounting interface and the load distributing rail securely mounts the first and second support assemblies to the load distributing plate along the load distributing rail, and wherein each of the first and second support assemblies is cantilevered over respective portions of the load distributing plate, such that the loads secured to the second ends of the respective first and second support assemblies are supported by the load distributing plate and suspended over the patient table.

20. The mounting assembly of claim 19, wherein the load secured to the second end of the first support assembly comprises a robotic medical device driver.

* * * * *

UNITED STATES PATENT AND TRADEMARK OFFICE
CERTIFICATE OF CORRECTION

PATENT NO. : 9,566,201 B2
APPLICATION NO. : 13/910903
DATED : February 14, 2017
INVENTOR(S) : Alan Lau Yu Page 1 of 1

It is certified that error appears in the above-identified patent and that said Letters Patent is hereby corrected as shown below:

In Column 9 at Line 18, Change "(1004)" to --(1004),--.

In Column 11 at Line 34, In Claim 17, after "assembly" delete "table".

Signed and Sealed this
Sixth Day of June, 2017

Michelle K. Lee
*Director of the United States Patent and Trademark Office*